United States Patent
Koehler et al.

(10) Patent No.: US 11,497,422 B2
(45) Date of Patent: Nov. 15, 2022

(54) INDICATOR AND ANALYTICS FOR SENSOR INSERTION IN A CONTINUOUS ANALYTE MONITORING SYSTEM AND RELATED METHODS

(71) Applicant: Dexcom, Inc., San Diego, CA (US)

(72) Inventors: Katherine Yerre Koehler, Solana Beach, CA (US); Leif N. Bowman, San Diego, CA (US); Rian Draeger, San Diego, CA (US); Laura Dunn, San Diego, CA (US); Eli Reihman, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 17/644,065

(22) Filed: Dec. 13, 2021

(65) Prior Publication Data
US 2022/0160267 A1    May 26, 2022

Related U.S. Application Data

(63) Continuation of application No. 16/440,852, filed on Jun. 13, 2019, now Pat. No. 11,197,626, which is a
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0022* (2013.01); *A61B 5/684* (2013.01);
(Continued)

(58) Field of Classification Search
None
See application file for complete search history.

(56) References Cited

U.S. PATENT DOCUMENTS 6,001,067 A    12/1999    Shults et al.
6,032,119 A *   2/2000    Brown .................... G06T 11/00
                                                              600/300

(Continued)

FOREIGN PATENT DOCUMENTS

WO    2012170000 A1    12/2012
WO    2013166426 A1    11/2013
WO    2014209552 A1    12/2014

OTHER PUBLICATIONS

Brackenridge B., et al., "Tape Tips and Other Infusion Site Information," Product Brochure, Minimed Technologies, 1995, 11 pages.
(Continued)

*Primary Examiner* — Fekadeselassie Girma
(74) *Attorney, Agent, or Firm* — Patterson + Sheridan, LLP

(57) ABSTRACT

The present embodiments provide systems and methods for, among others, tracking sensor insertion locations in a continuous analyte monitoring system. Data gathered from sensor sessions can be used in different ways, such as providing a user with a suggested rotation of insertion locations, correlating data from a given sensor session with sensor accuracy and/or sensor session length, and providing a user with a suggested next insertion location based upon past sensor accuracy and/or sensor session length at that location.

20 Claims, 16 Drawing Sheets

Related U.S. Application Data continuation of application No. 15/991,634, filed on May 29, 2018, now Pat. No. 10,368,786, which is a continuation of application No. 15/585,757, filed on May 3, 2017, now Pat. No. 10,004,437, which is a continuation of application No. 15/362,623, filed on Nov. 28, 2016, now Pat. No. 9,668,696, which is a continuation of application No. 15/224,306, filed on Jul. 29, 2016, now Pat. No. 9,717,445, which is a continuation of application No. 14/539,890, filed on Nov. 12, 2014, now Pat. No. 9,480,401.

(60) Provisional application No. 61/904,396, filed on Nov. 14, 2013.

(51) Int. Cl.
    *G16H 40/63*     (2018.01)
    *G16H 10/60*     (2018.01)
    *G16H 50/70*     (2018.01)
    *G06F 3/0481*     (2022.01)
    *H04L 67/125*     (2022.01)
    *G06T 7/70*     (2017.01)
    *G06F 3/04842*     (2022.01)
    *G06F 3/04883*     (2022.01)
    *G06F 3/0488*     (2022.01)

(52) U.S. Cl.
CPC .............. *A61B 5/743* (2013.01); *A61B 5/748* (2013.01); *G06F 3/0481* (2013.01); *G06T 7/70* (2017.01); *G16H 10/60* (2018.01); *G16H 40/63* (2018.01); *G16H 50/70* (2018.01); *H04L 67/125* (2013.01); *A61B 2560/0487* (2013.01); *G06F 3/0488* (2013.01); *G06F 3/04842* (2013.01); *G06F 3/04883* (2013.01); *G06T 2207/30196* (2013.01); *Y02A 90/10* (2018.01)

(56) References Cited

U.S. PATENT DOCUMENTS

| | | | |
|---|---|---|---|
| 6,068,599 A | 5/2000 | Saito et al. | |
| 6,618,047 B1 | 9/2003 | Lim | |
| 6,622,048 B1* | 9/2003 | Mann | A61N 1/36071 607/46 |
| 6,893,545 B2 | 5/2005 | Gotoh et al. | |
| 8,010,174 B2 | 8/2011 | Goode, Jr. et al. | |
| 8,260,393 B2 | 9/2012 | Kamath et al. | |
| 8,423,113 B2 | 4/2013 | Shariati et al. | |
| 8,593,453 B2* | 11/2013 | Sharp | A63F 13/10 345/419 |
| 8,860,717 B1* | 10/2014 | Zeiger | G06F 3/04847 345/419 |
| 9,211,092 B2 | 12/2015 | Bhavaraju et al. | |
| 9,283,053 B2* | 3/2016 | Mayse | A61B 34/30 |
| 9,480,401 B2 | 11/2016 | Koehler et al. | |
| 9,610,013 B2 | 4/2017 | Koehler et al. | |
| 9,668,696 B2 | 6/2017 | Koehler et al. | |
| 9,717,445 B2 | 8/2017 | Koehler et al. | |
| 10,004,437 B2 | 6/2018 | Koehler et al. | |
| 10,055,948 B2* | 8/2018 | Kim | G08B 6/00 |
| 10,226,207 B2* | 3/2019 | Stafford | A61B 5/1473 |
| 10,293,135 B2* | 5/2019 | Quigley | A61M 25/00 |
| 10,368,786 B2 | 8/2019 | Koehler et al. | |
| 10,433,773 B1* | 10/2019 | Budiman | A61B 5/14532 |
| 11,197,626 B2* | 12/2021 | Koehler | H04L 67/125 |
| 2002/0049362 A1* | 4/2002 | Ding | A61N 5/1048 600/1 |
| 2004/0122308 A1* | 6/2004 | Ding | A61N 5/1048 600/407 |
| 2005/0027463 A1 | 2/2005 | Goode, Jr. et al. | |
| 2005/0137464 A1* | 6/2005 | Bomba | A61B 5/6841 600/509 |
| 2005/0149363 A1* | 7/2005 | Loiterman | G16H 10/20 705/3 |
| 2006/0020187 A1 | 1/2006 | Brister et al. | |
| 2007/0027385 A1 | 2/2007 | Brister et al. | |
| 2008/0139903 A1 | 6/2008 | Bruce et al. | |
| 2009/0131968 A1* | 5/2009 | Birk | A61F 5/0046 606/192 |
| 2009/0137887 A1 | 5/2009 | Shariati et al. | |
| 2009/0157141 A1 | 6/2009 | Chiao et al. | |
| 2009/0192366 A1* | 7/2009 | Mensinger | G16H 40/63 706/14 |
| 2009/0326981 A1* | 12/2009 | Karkanias | G16H 40/63 705/3 |
| 2010/0149363 A1 | 6/2010 | Inomata et al. | |
| 2010/0185175 A1* | 7/2010 | Kamen | A61M 5/1723 604/67 |
| 2011/0027127 A1 | 2/2011 | Simpson et al. | |
| 2011/0184267 A1 | 7/2011 | Duke et al. | |
| 2011/0213225 A1 | 9/2011 | Bernstein et al. | |
| 2011/0224561 A1 | 9/2011 | Ashida | |
| 2011/0257495 A1* | 10/2011 | Hoss | A61B 5/1473 600/347 |
| 2011/0257496 A1 | 10/2011 | Terashima et al. | |
| 2012/0078071 A1 | 3/2012 | Bohm et al. | |
| 2012/0123230 A1* | 5/2012 | Brown | A61M 5/16804 600/347 |
| 2012/0127157 A1* | 5/2012 | Adler | G06Q 10/00 345/419 |
| 2012/0265035 A1 | 10/2012 | Bohm et al. | |
| 2013/0035575 A1* | 2/2013 | Mayou | G16H 50/70 600/365 |
| 2013/0093829 A1 | 4/2013 | Rosenblatt et al. | |
| 2013/0137952 A1* | 5/2013 | McCann | A61B 5/14532 600/365 |
| 2013/0231543 A1 | 9/2013 | Facchinetti et al. | |
| 2013/0245401 A1 | 9/2013 | Estes et al. | |
| 2014/0005505 A1 | 1/2014 | Peyser et al. | |
| 2014/0005508 A1 | 1/2014 | Estes et al. | |
| 2014/0005509 A1 | 1/2014 | Bhavaraju et al. | |
| 2014/0005531 A1 | 1/2014 | Taylor | |
| 2014/0036055 A1* | 2/2014 | Soma | G06T 7/74 348/77 |
| 2014/0104311 A1* | 4/2014 | Park | A61B 6/461 345/629 |
| 2014/0129151 A1* | 5/2014 | Bhavaraju | G16H 40/63 702/19 |
| 2014/0148665 A1* | 5/2014 | Bernstein | A61B 5/1495 600/365 |
| 2014/0182350 A1 | 7/2014 | Bhavaraju et al. | |
| 2014/0275898 A1 | 9/2014 | Taub et al. | |
| 2014/0276242 A1* | 9/2014 | Chen | A61B 5/1116 600/595 |
| 2014/0278189 A1* | 9/2014 | Vanslyke | G16H 40/40 702/104 |
| 2015/0130634 A1* | 5/2015 | Grubstein | A61B 5/743 340/870.07 |
| 2015/0135118 A1* | 5/2015 | Grubstein | A61B 5/684 715/771 |
| 2016/0166213 A1* | 6/2016 | Isaacson | A61B 5/14551 600/364 |
| 2016/0203275 A1 | 7/2016 | Benjamin et al. | |
| 2016/0270740 A1* | 9/2016 | Raisoni | A61B 5/1459 |
| 2016/0345874 A1* | 12/2016 | Raisoni | A61B 5/0022 |
| 2016/0364547 A1 | 12/2016 | Love et al. | |
| 2017/0095185 A1* | 4/2017 | Okuyama | A61B 5/0004 |
| 2019/0073012 A1* | 3/2019 | Sultenfuss | H02J 7/0068 |
| 2019/0094937 A1* | 3/2019 | Sultenfuss | G06F 1/26 |
| 2019/0147140 A1* | 5/2019 | Rudser | G16H 40/40 705/2 |
| 2019/0392688 A1* | 12/2019 | Choi | G06F 3/016 |
| 2020/0008758 A1* | 1/2020 | Di Resta | A61B 5/7425 |
| 2020/0015719 A1 | 1/2020 | Koehler et al. | |

(56) References Cited

OTHER PUBLICATIONS

Extended European Search Report for Application No. 20194868.4 dated Apr. 12, 2021, 8 pages.
International Preliminary Report on Patentability for Application No. PCT/US2014/065306 dated May 26, 2016, 14 pages.
International Search Report and Written Opinion for Application No. PCT/US2014/065306 dated Mar. 31, 2015, 19 pages.

* cited by examiner

INDICATOR AND ANALYTICS FOR SENSOR INSERTION IN A CONTINUOUS ANALYTE MONITORING SYSTEM AND RELATED METHODS

CROSS-REFERENCE TO RELATED APPLICATIONS

This application is a continuation of U.S. patent application Ser. No. 16/440,852, filed Jun. 13, 2019, which is a continuation of U.S. patent application Ser. No. 15/991,634, filed May 29, 2018, which is a continuation of U.S. patent application Ser. No. 15/585,757, filed May 3, 2017, which is a continuation of U.S. patent application Ser. No. 15/362,623, filed Nov. 28, 2016, which is a continuation of U.S. patent application Ser. No. 15/224,306, filed Jul. 29, 2016, which is a continuation of U.S. patent application Ser. No. 14/539,890, filed Nov. 12, 2014, which claims the benefit of U.S. Provisional Application No. 61/904,396, filed Nov. 14, 2013, the entire contents of each of which are incorporated by reference herein.

TECHNICAL FIELD

The present embodiments relate to continuous analyte monitoring, and, in particular, to placement of a sensor of a continuous analyte monitoring system on the body of the user.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdoes of insulin, or after a normal dose of insulin or glucose-lowering agent accompanied by extraordinary exercise or insufficient food intake.

Conventionally, a person with diabetes carries a self-monitoring blood glucose (SMBG) monitor, which typically required uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter that transmits measurement data to a receiver that processes and displays information based on the measurements. Such sensor systems are sometimes referred to as continuous glucose monitors (CGMs).

SUMMARY

The present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

A sensor of a CGM system is implanted through the skin of the host. When the sensor has reached the limit of its lifespan, it is removed and a new sensor is inserted. A typical sensor lifespan is anywhere from a few days to one week or more. Users of CGM systems thus insert a new sensor sometimes as often as every few days. Because the sensor penetrates the skin, repeated sensor insertion in the same location can lead to scarring. Thus, it can be desirable to vary the location for each new sensor insertion. However, the effectiveness of the sensor may be impacted by the location where it is implanted, because the composition of the host's body varies from one location to another, including factors such as fat concentration, skin thickness, presence of capillaries, muscle tissue, body heat, skin perspiration at the site, scarring, thickness of skin, blood flow, movement of the location, vascularization, muscle movement, exposure to external elements/temperature (e.g., wrist vs. abdomen), insulin pump infusion sites, tattoos, rash or other skin conditions such as eczema or psoriasis Thus, it would be desirable to track information related to sensor insertion site location, for example, to know what location(s) on a given host's body are most likely to achieve the best CGM results.

In a first aspect, which is generally applicable (i.e. independently combinable with any of the aspects or embodiments identified herein), particularly with any other embodiment of the first aspect, certain of the present embodiments comprise a method for continuous analyte monitoring including a continuous analyte monitoring system having a sensor. The method comprises initiating a new sensor session with a transmitter and a device having a display. The method further comprises displaying a diagram of a body on the display. The method further comprises receiving as an input, via the diagram, a location on the body where the sensor was inserted into skin of a host. The method further comprises storing the location.

In an embodiment of the first aspect, the method further comprises correlating data from the sensor for the sensor session with the location.

In an embodiment of the first aspect, the method further comprises storing the correlated data.

In an embodiment of the first aspect, the method further comprises transmitting the correlated data to a database, the database including other correlated data associated with other hosts.

In an embodiment of the first aspect, the data includes quantitative data regarding one or more sensor sessions corresponding to one or more sensor insertion locations.

In an embodiment of the first aspect, the quantitative data comprises at least one of sensor accuracy, sensor session length, sensor baseline, sensor sensitivity, sensor sensitivity decline over time, sensor performance vs. past performance in a same person, sensor performance vs. a population of users, sensor performance by days or wear, sensor performance by geographical location, sensor performance by external environment, sensor performance by activity level, data indicative of signal noise, time spent out of communication range, adhesive data, reliability, data capture, noise metrics, detected faults, end of life metrics, and confidence levels.

In an embodiment of the first aspect, the method further comprises receiving as an input personal information of the host.

In an embodiment of the first aspect, the personal information includes at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, or adhesive success rate.

In a second aspect, which is generally applicable (i.e. independently combinable with any of the aspects or embodiments identified herein), particularly with any other embodiment of the second aspect, certain of the present embodiments comprise a method for continuous analyte monitoring including a continuous analyte monitoring system having a sensor. The method comprises initiating a new sensor session with a transmitter and a device having a display and a camera. The method further comprises receiving as an input, via the camera, a photograph of a location on a body where the sensor was inserted into skin of a host. The method further comprises analyzing the photograph to determine the location. The method further comprises storing the location.

In an embodiment of the second aspect, the method further comprises correlating data from the sensor for the sensor session with the location.

In an embodiment of the second aspect, the method further comprises storing the correlated data.

In an embodiment of the second aspect, the method further comprises transmitting the correlated data to a database, the database including other correlated data associated with other hosts.

In an embodiment of the second aspect, the data includes quantitative data regarding one or more sensor sessions corresponding to one or more sensor insertion locations.

In an embodiment of the second aspect, the quantitative data comprises at least one of sensor accuracy, sensor session length, sensor baseline, sensor sensitivity, sensor sensitivity decline over time, sensor performance vs. past performance in a same person, sensor performance vs. a population of users, sensor performance by days or wear, sensor performance by geographical location, sensor performance by external environment, sensor performance by activity level, data indicative of signal noise, time spent out of communication range, adhesive data, reliability, data capture, noise metrics, detected faults, end of life metrics, and confidence levels.

In an embodiment of the second aspect, the method further comprises receiving as an input personal information of the host.

In an embodiment of the second aspect, the personal information includes at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, or adhesive success rate.

In a third aspect, which is generally applicable (i.e. independently combinable with any of the aspects or embodiments identified herein), particularly with any other embodiment of the third aspect, certain of the present embodiments comprise a method for continuous analyte monitoring. The method comprises displaying, on a device having a display, a diagram of a body, the diagram indicating at least one location on the body where a sensor of a continuous analyte monitoring system was previously inserted. The method further comprises displaying, on the display, information about each location.

In an embodiment of the third aspect, the information includes a date when the sensor was inserted at each location.

In an embodiment of the third aspect, the information includes quantitative data regarding one or more sensor sessions associated with each location.

In an embodiment of the third aspect, the quantitative data comprises at least one of sensor accuracy, sensor session length, sensor baseline, sensor sensitivity, sensor sensitivity decline over time, sensor performance vs. past performance in a same person, sensor performance vs. a population of users, sensor performance by days or wear, sensor performance by geographical location, sensor performance by external environment, sensor performance by activity level, data indicative of signal noise, time spent out of communication range, adhesive data, reliability, data capture, noise metrics, detected faults, end of life metrics, and confidence levels.

In a fourth aspect, which is generally applicable (i.e. independently combinable with any of the aspects or embodiments identified herein), particularly with any other embodiment of the fourth aspect, certain of the present embodiments comprise a method for continuous analyte monitoring. The method comprises downloading, to a device having a display, data regarding one or more sensor sessions associated with a plurality of hosts, the data being correlated with a location of each of the sensor sessions. The method further comprises displaying, on the display, the correlated data.

In an embodiment of the fourth aspect, the method further comprises providing a suggested sensor insertion location on a body of a host, based on the correlated data.

In an embodiment of the fourth aspect, the correlated data comprises at least one of sensor accuracy, sensor session length, sensor baseline, sensor sensitivity, sensor sensitivity decline over time, sensor performance vs. past performance in a same person, sensor performance vs. a population of users, sensor performance by days or wear, sensor performance by geographical location, sensor performance by external environment, sensor performance by activity level, data indicative of signal noise, time spent out of communication range, adhesive data, reliability, data capture, noise metrics, detected faults, end of life metrics, and confidence levels correlated with each location.

In a fifth aspect, which is generally applicable (i.e. independently combinable with any of the aspects or embodiments identified herein), particularly with any other embodiment of the fifth aspect, certain of the present embodiments comprise a system for continuous analyte monitoring. The system comprises an electronic device having a display and storing executable instructions. The system further comprises a continuous analyte sensor configured to be implanted within a body. The system further comprises sensor electronics configured to receive and process sensor data output by the sensor, to initialize the sensor, and to transmit a signal to the electronic device. Upon insertion of the sensor into skin of the host, a new sensor session is initiated with the sensor electronics and the electronic device, and the electronic device executes the executable instructions to display a diagram of a body on the display.

In an embodiment of the fifth aspect, the electronic device is configured to receive as an input, via the diagram, a location on the body where the sensor was inserted.

In an embodiment of the fifth aspect, the electronic device is configured to store the location.

In an embodiment of the fifth aspect, the electronic device is configured to correlate data from the sensor for the sensor session with the location.

In an embodiment of the fifth aspect, the electronic device is configured to store the correlated data.

In an embodiment of the fifth aspect, the electronic device is configured to transmit the correlated data to a database, the database including other correlated data associated with other hosts.

In an embodiment of the fifth aspect, the electronic device is configured to receive as an input personal information of the host.

In an embodiment of the fifth aspect, the personal information includes at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, or adhesive success rate.

In an embodiment of the fifth aspect, the electronic device is a smartphone.

In an embodiment of the fifth aspect, the executable instructions comprise a downloadable application.

In a sixth aspect, which is generally applicable (i.e. independently combinable with any of the aspects or embodiments identified herein), particularly with any other embodiment of the sixth aspect, certain of the present embodiments comprise a system for continuous analyte monitoring. The system comprises an electronic device having a display and a camera, and storing executable instructions. The system further comprises a continuous analyte sensor configured to be implanted within a body. The system further comprises sensor electronics configured to receive and process sensor data output by the sensor, to initialize the sensor, and to transmit a signal to the electronic device. Upon insertion of the sensor into skin of a host, a new sensor session is initiated with the sensor electronics and the electronic device. The electronic device receives as an input, via the camera, a photograph of a location on the body where the sensor was inserted into the skin of the host, and the electronic device stores the location.

In an embodiment of the sixth aspect, the electronic device is configured to correlate data from the sensor for the sensor session with the location.

In an embodiment of the sixth aspect, the electronic device is configured to store the correlated data.

In an embodiment of the sixth aspect, the electronic device is configured to transmit the correlated data to a database, the database including other correlated data associated with other hosts.

In an embodiment of the sixth aspect, the electronic device is configured to receive as an input personal information of the host.

In an embodiment of the sixth aspect, the personal information includes at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, or adhesive success rate.

In an embodiment of the sixth aspect, the electronic device is a smartphone.

In an embodiment of the sixth aspect, the executable instructions comprise a downloadable application.

In a seventh aspect, which is generally applicable (i.e. independently combinable with any of the aspects or embodiments identified herein), particularly with any other embodiment of the seventh aspect, certain of the present embodiments comprise a method for continuous analyte monitoring. The method comprises displaying, on a device having a display, a diagram of a body. The method further comprises indicating, on the diagram, a recommended location for insertion of a sensor.

In an embodiment of the seventh aspect, the method further comprises performing a pattern analysis of data relating to previous sensor insertion locations.

In an embodiment of the seventh aspect, the data includes data pertaining to at least one other user.

In an eighth aspect, which is generally applicable (i.e. independently combinable with any of the aspects or embodiments identified herein), particularly with any other embodiment of the eighth aspect, certain of the present embodiments comprise a method for continuous analyte monitoring. The method comprises receiving as an input an insertion location on a body where a sensor of a continuous analyte monitoring system was inserted into skin of a host. The method further comprises storing the insertion location. The method further comprises receiving as inputs data relating to a sensor session of the sensor. The method further comprises correlating the data with the insertion location.

In an embodiment of the eighth aspect, the method further comprises providing a recommendation for a next insertion location based on the correlated data.

In an embodiment of the eighth aspect, the method further comprises storing the correlated data.

In an embodiment of the eighth aspect, the method further comprises transmitting the correlated data to a database, the database including other correlated data associated with other hosts.

In an embodiment of the eighth aspect, a remote computing device performs at least one of the steps of storing the insertion location, receiving as inputs data relating to a sensor session of the sensor, and correlating the data with the insertion location.

In an embodiment of the eighth aspect, the data pertains to at least one of sensor accuracy, sensor session length, sensor baseline, sensor sensitivity, sensor sensitivity decline over time, sensor performance vs. past performance in a same person, sensor performance vs. a population of users, sensor performance by days or wear, sensor performance by geographical location, sensor performance by external environment, sensor performance by activity level, data indicative of signal noise, time spent out of communication range, adhesive data, reliability, data capture, noise metrics, detected faults, end of life metrics, and confidence levels.

In an embodiment of the eighth aspect, the method further comprises receiving as an input personal information of the host.

In an embodiment of the eighth aspect, the personal information includes at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, or adhesive success rate.

In a ninth aspect, which is generally applicable (i.e. independently combinable with any of the aspects or embodiments identified herein), particularly with any other embodiment of the ninth aspect, certain of the present embodiments comprise a device substantially as shown and/or described in the specification and/or drawings.

In a tenth aspect, which is generally applicable (i.e. independently combinable with any of the aspects or embodiments identified herein), particularly with any other embodiment of the tenth aspect, certain of the present embodiments comprise a method substantially as shown and/or described in the specification and/or drawings.

In an eleventh aspect, which is generally applicable (i.e. independently combinable with any of the aspects or embodiments identified herein), particularly with any other embodiment of the eleventh aspect, certain of the present embodiments comprise a system substantially as shown and/or described in the specification and/or drawings.

BRIEF DESCRIPTION OF THE DRAWINGS

The present embodiments now will be discussed in detail with an emphasis on highlighting the advantageous features. These embodiments depict the novel and non-obvious indicator and analytics for sensor insertion in a continuous analyte monitoring system and related methods shown in the accompanying drawings, which are for illustrative purposes only. These drawings include the following figures, in which like numerals indicate like parts.

DETAILED DESCRIPTION

Figure 1:
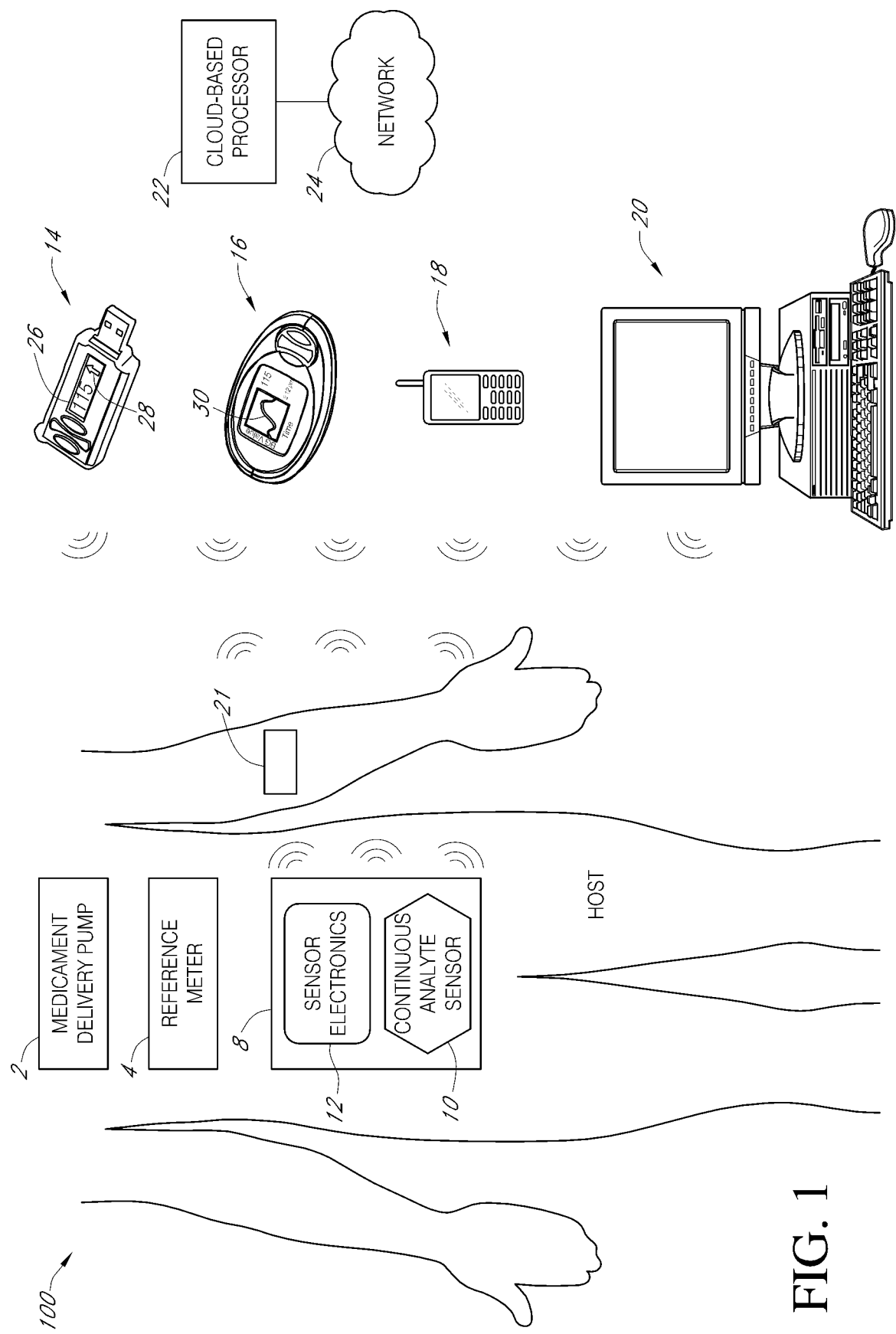
FIG. 1 is a schematic view of a continuous analyte sensor system attached to a host and communicating with other devices.

The following detailed description describes the present embodiments with reference to the drawings. In the drawings, reference numbers label elements of the present embodiments. These reference numbers are reproduced below in connection with the discussion of the corresponding drawing features.

The preferred embodiments relate to the use of an analyte sensor that measures a concentration of glucose or a substance indicative of the concentration or presence of the analyte. In some embodiments, the analyte sensor is a continuous device, for example a subcutaneous, transdermal, transcutaneous, and/or intravascular (e.g., intravenous) device. In some embodiments, the device can analyze a plurality of intermittent blood samples. The analyte sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The analyte sensor can use any known method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of the preferred embodiments can be applied to any measurable analyte. In some preferred embodiments, the analyte sensor is a glucose sensor capable of measuring the concentration of glucose in a host. One example embodiment is described below, which utilizes an implantable glucose sensor. However, it should be understood that the devices and methods described herein can be applied to any device capable of detecting a concentration of analyte and providing an output signal that represents the concentration of the analyte.

In one preferred embodiment, the analyte sensor is an implantable glucose sensor, such as described with reference to U.S. Pat. No. 6,001,067 and U.S. Publ. No. 2011-0027127-A1. In another preferred embodiment, the analyte sensor is a transcutaneous glucose sensor, such as described with reference to U.S. Publ. No. 2006-0020187-A1. In yet another preferred embodiment, the analyte sensor is a dual electrode analyte sensor, such as described with reference to U.S. Publ. No. 2009-0137887-A1. In still other embodiments, the sensor is configured to be implanted in a host vessel or extracorporeally, such as is described in U.S. Publ. No. 2007-0027385-A1.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to lactate or lactic acid; cardiac markers; ketone bodies; acetone; acetoacetic acid; beta hydroxybutyric acid; glucagon, acetyl Co A; intermediaries in the Citric Acid Cycle; choline, testosterone; creatinine; triglycerides; sodium; potassium; chloride; bicarbonate; total protein; alkaline phosphatase; calcium; phosphorus; $PO_2$; $PCO_2$; bilirubin (direct and total); red blood cell count; white blood cell count; hemoglobin; hemactocrit; lymphocytes; monocytes; eosinophils; basophils; c-reactive protein; cryoglobulins; fibrinogens; ACTH; aldosterone; ammonia; beta-HCG; magnesium; copper; iron; total cholesterol; low density lipoproteins; high density lipoproteins; lipoprotein A; T4 (total and free); TSH; FSH; LH; ACTH; hepatitis BE antigen; hepatitis B surface antigen; hepatitis A antibody; hepatitis C antibody; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diphtheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

For illustrative purposes, reference will now be made to FIG. 1, which is an example environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate to sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18, 20, and/or one or more wearable devices 21.

The system 100 of FIG. 1 also includes a cloud-based processor 22 configured to analyze analyte data, medicament delivery data, and/or other patient related data provided over network 24 directly or indirectly from one or more of sensor system 8, medicament delivery pump 2, reference analyte meter 4, display devices 14, 16, 18, 20, and wearable device 21. Based on the received data, the processor 22 can further process the data, generate reports providing information based on the processed data, trigger notifications to electronic devices associated with the host or caretaker of the host, or provide processed information to any of the other devices of FIG. 1. In some example implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

It should be understood that although the example implementation described with respect to FIG. 1 refers to analyte data being received by processor 22, other types of data processed and raw data may be received as well.

In some example implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, 20, and wearable device 21. The display devices 14, 16, 18, 20 may be configured for processing and presenting information, such as sensor information transmitted by the sensor electronics module 12 for display at the display device. The display devices 14, 16, 18, 20, and/or the wearable device 21 may also trigger alarms based on the analyte sensor data.

The wearable device 21 may also be configured for processing and presenting information, such as sensor information transmitted by the sensor electronics module 12. The wearable device 21 may include an alert interface. The alert interface may comprise, for example, a display, a vibration module, a shock module, a speaker, and/or any other type of device that is capable of providing the user with physiological information.

In FIG. 1, display device 14 is a key fob-like display device, display device 16 is a hand-held application-specific computing device 16 (e.g. the DexCom G4® Platinum receiver commercially available from DexCom, Inc.), display device 18 is a general purpose smart phone or tablet computing device 20 (e.g. an Apple® iPhone®, iPad®, or iPod Touch® commercially available from Apple, Inc.), display device 20 is a computer workstation 20, and wearable device 21 is any device that is worn on, or integrated into, a user's vision, clothes, and/or bodies. In some example implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. In some example implementations, the wearable device 21 may comprise anklets, glasses, rings, necklaces, arm bands, pendants, belt clips, hair clips/ties, pins, cufflinks, tattoos, stickers, socks, sleeves, gloves, garments (e.g. shirts, pants, underwear, bra, etc.), "clothing jewelry" such as zipper pulls, buttons, watches, shoes, contact lenses, subcutaneous implants, cochlear implants, shoe inserts, braces (mouth), braces (body), medical wrappings, sports bands (wrist band, headband), hats, bandages, hair weaves, nail polish, artificial joints/body parts, orthopedic pins/devices, implantable cardiac or neurological devices, etc. The small display device 14 and/or the wearable device 21 may include a relatively small display (e.g., smaller than the display device 18) and may be configured to display graphical and/or numerical representations of sensor information, such as a numerical value 26 and/or an arrow 28. In contrast, the display devices 16, 18, and 20 can be larger display devices that can be capable of displaying a larger set of displayable information, such as a trend graph 30 depicted on the hand-held receiver 16 in addition to other information such as a numerical value and arrow.

In various embodiments, the wearable device 21 may be attached to the wearer and/or to his or her clothing in any convenient fashion. For example, the wearable device 21 may encompass a body part of the wearer, such as an arm, a leg, the neck, etc. instead, or in addition, the wearable device 21 may be secured to the wearer's skin with adhesive. In embodiments including a vibration module, a shock module, or any other device that provides the wearer with tactile feedback, these embodiments may be most effective if the wearable device 21 is directly or indirectly touching the wearer's skin in such a way that vibrations, shocks, etc. can be felt by the wearer. For example, directly securing the wearable device 21 to the wearer's skin with adhesive may be advantageous.

It is understood that any other user equipment (e.g. computing devices) configured to at least present information (e.g., a medicament delivery information, discrete self-monitoring monitoring analyte readings, heart rate monitor, caloric intake monitor, and the like) can be used in addition or instead of those discussed with reference to FIG. 1.

In some example implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations of FIG. 1, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

A sensor of a CGM system is implanted through the skin of the host. When the sensor has reached the limit of its lifespan, it is removed and a new sensor is inserted. A typical sensor lifespan is anywhere from a few days to one week or more. Users of CGM systems thus insert a new sensor sometimes as often as every few days. Because the sensor penetrates the skin, repeated sensor insertion in the same location can lead to scarring. Thus, it can be desirable to vary the location for each new sensor insertion. However, the effectiveness of the sensor may be impacted by the location where it is implanted, because the composition of the host's body varies from one location to another, including factors such as fat concentration, skin thickness, presence of capillaries, muscle tissue, body heat, skin perspiration at the site, scarring, blood flow, movement of the location, vascularization, muscle movement, exposure to external elements/temperature (e.g., wrist vs. abdomen), insulin pump infusion sites, tattoos, rash or other skin conditions such as eczema or psoriasis, etc. Daily activities may also affect the insertion site, such as seatbelt location/usage, repetitive movement (e.g., exercise-related or work-related movements), normal sedentary positions (e.g., yoga, sleeping or sitting positions), or pressure from external factors, such as a uniform. Thus, it would be desirable to know what location(s) on a given host's body are most likely to achieve the best CGM results.

Figure 2A:
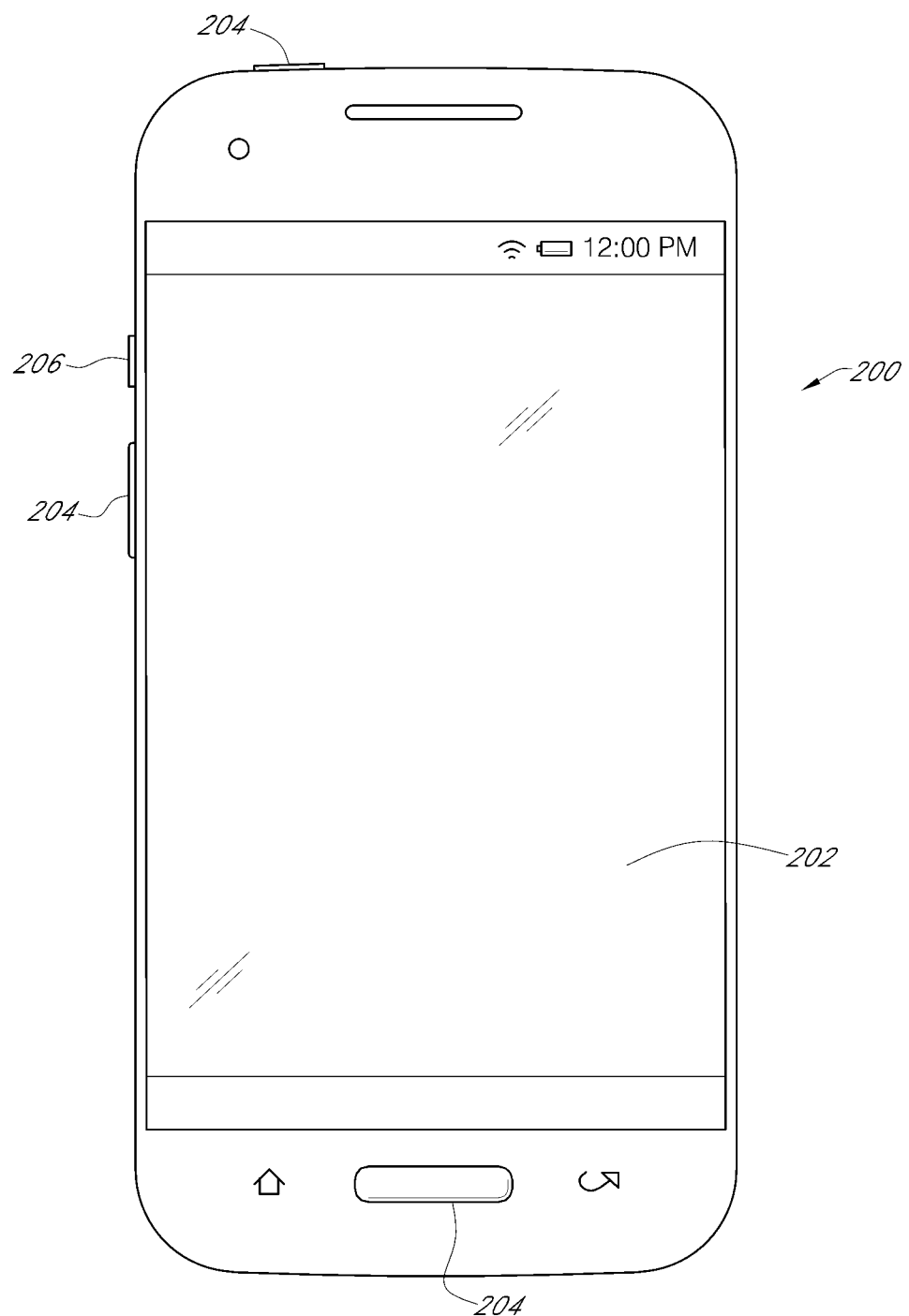
FIG. 2A is a front elevation view of an electronic device configured for use with the present systems and methods.

FIG. 2A illustrates one embodiment of an electronic device 200 configured for use with the present systems and methods. The electronic device 200 includes a display 202 and one or more input/output (I/O) devices, such as one or more buttons 204 and/or switches 206. In the illustrated embodiment, the electronic device 200 is a smartphone, and the display 202 comprises a touchscreen, which also functions as an I/O device. In other embodiments, the electronic device 200 may comprise a device or devices other than a smartphone, such as a receiver of a CGM system, a smartwatch, a tablet computer, a mini-tablet computer, a handheld personal data assistant (PDA), a game console, a multimedia player, a wearable device, such as those described above, a screen in an automobile, etc. While the electronic device 200 is illustrated as a smartphone in the figures, the electronic device 200 can be any of the other electronic devices mentioned herein and/or incorporate the functionality of any or all of the other electronic devices, including wherein some or all of the functionally is embodied on a remote server.

Figure 2B:
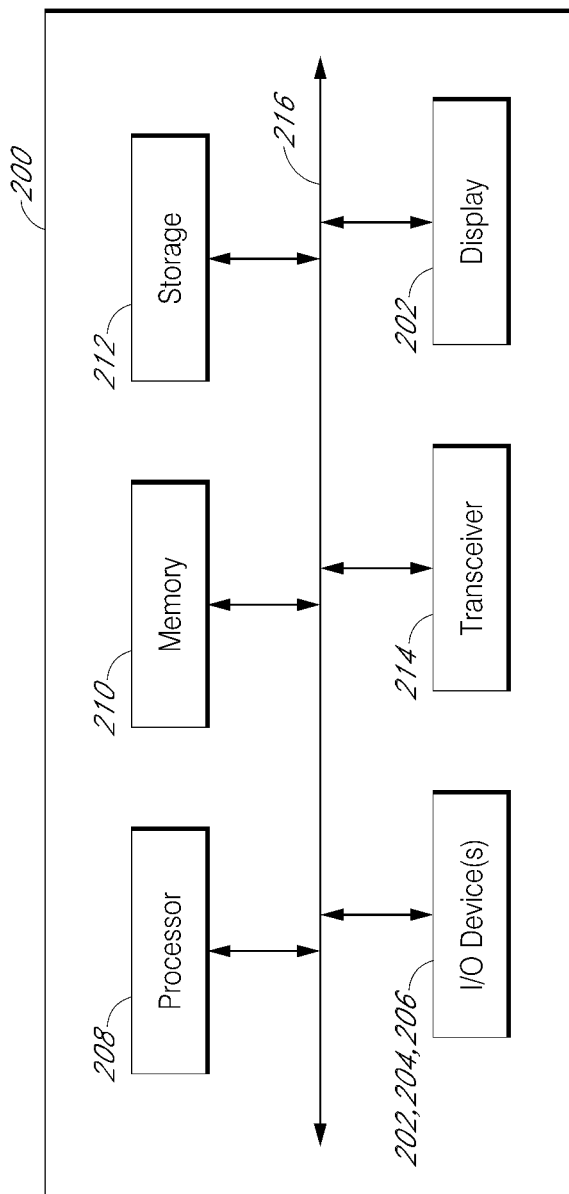
FIG. 2B is a functional block diagram of the electronic device of FIG. 2A.

FIG. 2B is a block diagram of the electronic device 200 shown in FIG. 2A, illustrating its functional components in accordance with some embodiments. The electronic device 200 includes the display 202 and one or more input/output ("I/O") device(s) 204, 206, as described above with respect to FIG. 2A. The display 202 may be any device capable of displaying output, such as an LCD or LED screen and others. The input/output (I/O) devices 202, 204, 206 may comprise, for example, a keyboard (not shown), one or more buttons 204, one or more switches 206, etc. In embodiments including a touchscreen, the display 202 also functions as an I/O device.

The electronic device 200 further includes a processor 208 (also referred to as a central processing unit (CPU)), a memory 210, a storage device 212, a transceiver 214, and may include other components or devices (not shown). The memory 210 is coupled to the processor 208 via a system bus or a local memory bus 216. The processor 208 may be, or may include, one or more programmable general-purpose or special-purpose microprocessors, digital signal processors (DSPs), programmable controllers, application specific integrated circuits (ASICs), programmable logic devices (PLDs), or the like, or a combination of such hardware-based devices.

The memory 210 provides the processor 208 access to data and program information that is stored in the memory 210 at execution time. Typically, the memory 210 includes random access memory (RAM) circuits, read-only memory (ROM), flash memory, or the like, or a combination of such devices.

The storage device 212 may comprise one or more internal and/or external mass storage devices, which may be or may include any conventional medium for storing large volumes of data in a non-volatile manner. For example, the storage device 212 may include conventional magnetic disks, optical disks, magneto-optical (MO) storage, flash-based storage devices, or any other type of non-volatile storage devices suitable for storing structured or unstructured data. The storage device 212 may also comprise storage in the "cloud" using so-called cloud computing. Cloud computing pertains to computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction.

The electronic device 200 may perform various processes, such as, for example, correlating data, pattern analysis, and other processes. In some embodiments, the electronic device 200 may perform such processes on its own. Alternatively, such processes may be performed by one or more other devices, such as one or more cloud-based processors 22 described above. In still further embodiments, these processes may be performed in part by the electronic device 200 and in part by other devices. Various example processes are described herein with reference to the electronic device 200. It should be understood that these example processes are not limited to being performed by the electronic device 200 alone. Further, as used herein, the term "electronic device" should be construed to include other devices with which the electronic device 200 interacts, such as one or more cloud-based processors, servers, etc.

The electronic device 200 may also include other devices/interfaces for performing various functions. For example, the electronic device 200 may include a camera (not shown).

The transceiver 214 enables the electronic device 200 to communicate with other computing systems, storage devices, and other devices via a network. While the illustrated embodiment includes a transceiver 214, in alternative embodiments a separate transmitter and a separate receiver may be substituted for the transceiver 214.

In some embodiments, the processor 208 may execute various applications, for example, a CGM application, which may be downloaded to the electronic device 200 over the Internet and/or a cellular network, and the like. Data for various applications may be shared between the electronic device 200 and one or more other devices/systems, and stored by storage 212 and/or on one or more other devices/systems.

In certain of the present embodiments, the sensor 10 of the continuous analyte sensor system 8 of FIG. 1 is inserted into the skin of a host. A new sensor session is then initiated with the sensor 10, the sensor electronics 12, and the electronic device 200. The embodiments described herein contemplate numerous techniques for initializing the sensor 10. For example, initialization may be triggered when the sensor electronics 12 engages the sensor 10. In another example, initialization may be triggered by a mechanical switch, such as a switch (not shown) on a snap-in base that receives the sensor electronics 12. When the sensor electronics 12 are snapped into the base, the switch is automatically tripped. In another example, initialization may be menu driven, as the user may be prompted by a user interface on the display 202 of the electronic device 200 to begin initialization by making a selection on the user interface, such as by pushing a button or touching a designated area on a display 202 (which may comprise a touchscreen). In another example involving a non-invasive sensor that is applied to the wearer's skin, the sensor 10 may sense when it is in contact with skin and start automatically. Further, the analyte sensor system 8 can detect use of a new sensor 10 using any of the above techniques, automatically prompt the user to confirm the new sensor session by way of a prompt on a user interface of the system 8, and initiate an initialization response to the user confirmation responsive to the prompt. Additional examples of initializing the sensor 10 are found in U.S. Publ. No. 2013-0245401-A1, the entire disclosure of which is hereby incorporated by reference herein.

Figure 3:
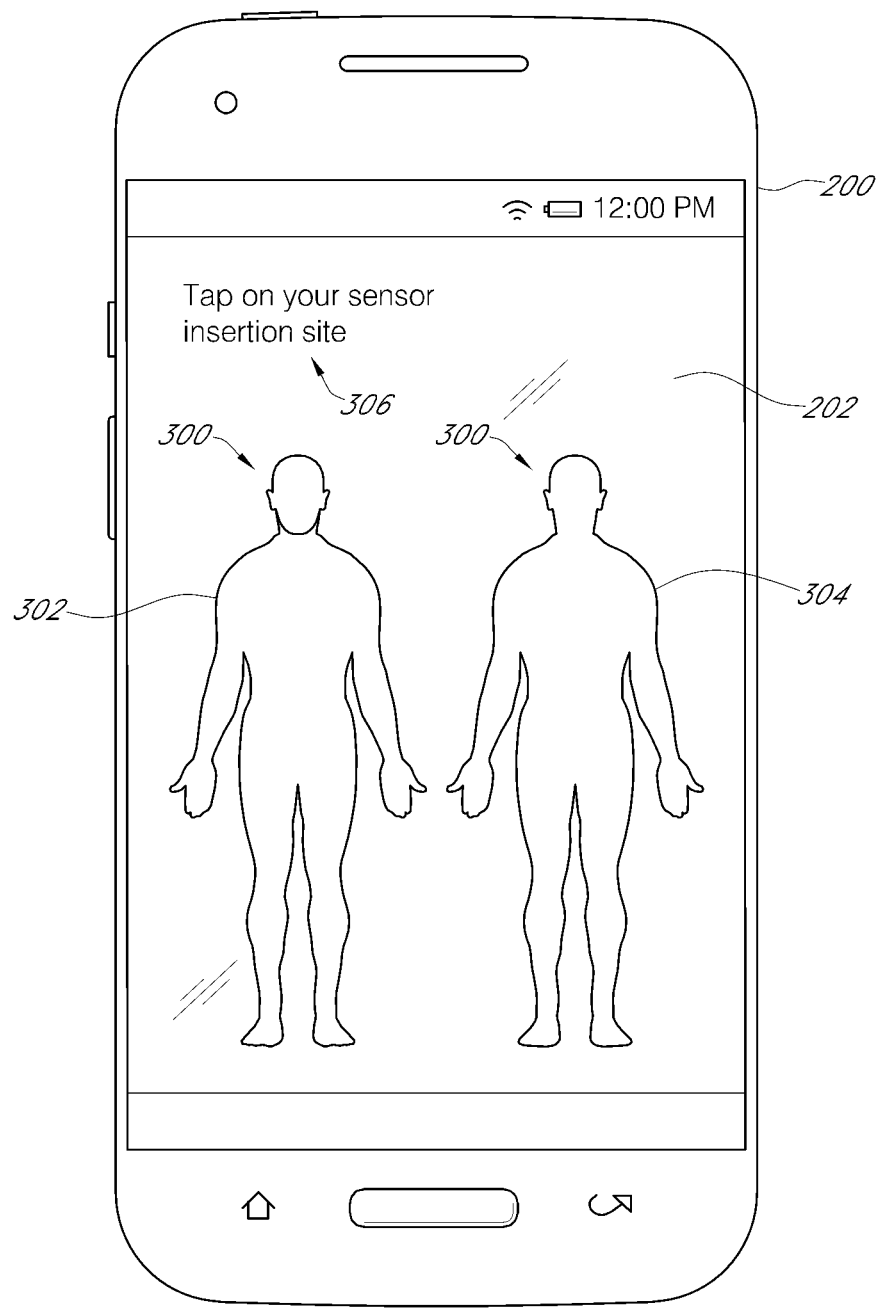
FIGS. 3-6 are front elevation views of the electronic device of FIG. 2A, illustrating various embodiments of a user interface.

FIG. 3 illustrates an example of a user interface for tracking locations of sensor insertion locations. When a new sensor session starts, the user interface of FIG. 3 may be shown on the display 202. The present embodiments contemplate numerous techniques for causing the user interface of FIG. 3 to be shown on the display 202. For example, when the sensor electronics are powered on, the sensor electronics may send a signal to any electronic device within range of the sensor electronics, and the signal may prompt the electronic device to execute instructions stored in the electronic device that cause the user interface of FIG. 3 to appear on the display 202. In another example, the user may initiate communication between the sensor electronics and the electronic device by inputting one or more commands to the electronic device. For example, if the electronic device is a smartphone, and the executable instructions stored in the electronic device comprise an application, such as a downloadable application, the user may launch the application. The user interface of FIG. 3 would then be shown on the display 202. In another example, the user interface of FIG. 3 may be shown on the display 202 before a new sensor is inserted, such as when a previous sensor session ends, which may coincide with an expiration of the previous sensor, or upon opening the CGM application when no sensor is currently inserted in the host and/or communicating with the CGM application.

As shown in FIG. 3, the user interface comprises a diagram 300 of a body. In the illustrated embodiment, both a front view 302 and a back view 304 of the body 300 are shown, but in alternative embodiments only one or the other may be shown. In some embodiments, the user may input, via the diagram 300, a location on the body where the sensor was inserted. The electronic device 200 may then store the input location. For example, where the display 202 is a touchscreen, the user may tap on the diagram 300 in the location on the body where the sensor was inserted. The display 202 may also provide text 306, such as instructions for the user. For example, in FIG. 3 the display 202 indicates that the user should tap on (or otherwise indicate) the location on the body where the sensor was inserted.

In some embodiments, the display 202 may show a draggable icon of a sensor, and the user may select the icon and drag it to the location on the diagram 300 where the sensor was inserted. Also in some embodiments, a template may be provided, for example, inside packaging or printed on packaging associated with a new sensor or another component of a CGM system. Alternatively, the template may be downloadable from a website on the Internet. The template may include a diagram of a body, which may be similar to the diagram 300 discussed above. The diagram may have various sensor insertion sites identified, for example with label(s) and/or x-y coordinates. To input a location where a user has inserted a new sensor, the user may input into the electronic device the label and/or coordinates of the insertion site as indicated on the diagram.

In certain embodiments, each time the user begins a new sensor session, he or she inputs into the electronic device the location of sensor insertion, and the electronic device stores this information. Data pertaining to the sensor insertion locations may be used in many different ways, according to the present embodiments. For example, quantitative data for each sensor session may be correlated with the sensor insertion location of each location. Quantitative data correlated with sensor insertion location may be, for example, sensor accuracy (e.g., a mean absolute relative difference (MARD) or other statistical measure of accuracy), sensor session length, sensor baseline, sensor sensitivity, sensor sensitivity decline over time, sensor performance vs. past performance in the same person, sensor performance vs. a larger population of users to figure out if a user is typical or atypical in how the sensor performs in him or her, sensor performance by days or wear, sensor performance by geographical location, sensor performance by external environment (e.g. temperature, humidity), sensor performance by activity level, data indicative of signal noise, time spent out of communication range (e.g. because of a broken antenna), adhesive data (e.g. data obtained from user when an adhesive associated with the sensor falls off the skin), reliability, data capture, noise metrics, detected faults, end of life metrics, confidence levels, etc. Collected data may be compared with data from other users in a network based on demographics, such as zip code, age, etc. Qualitative data may include a rating system, number of starts (e.g., out of 5), thumbs up/down, user impression, etc. The correlation may include consideration of additional factors, such as, for example, the user's body temperature, the user's sleep cycle, what side the user sleeps on and/or how long the user sleeps on each side on average, or any other biometric data of the user.

With respect to sensor session length, although commercial sensors are labeled for a predetermined sensor session duration (e.g., 3 days, 5 days, 7 days, 10 days, etc), it is not uncommon for the useful life of a commercial sensor to end before the predetermined sensor session duration. After the useful life, the sensor may no longer be reliable, providing inaccurate sensor data. To prevent use beyond the useful life, some embodiments notify a user to change the sensor after it has been determined that the sensor should no longer be used. Various methods can be used to determine whether a sensor should no longer be used, such as a predetermined amount of time transpiring since the sensor was first used (e.g., when first implanted into a user or when first electrically connected to sensor electronics) or a determination that the sensor is defective (e.g., due to membrane rupture, unstable sensitivity, or the like). Once it is determined that the sensor should no longer be used, the sensor system can notify a user that a new sensor should be used by audibly and/or visually prompting a user to use a new sensor and/or shutting down the display 202 or ceasing to display new (or real-time) sensor data on the display 202, for example. In some embodiments, continuous glucose monitors may show signs of sensor "end of life" near their end of life. The signs of end of life may be recognized and total sensor end of life and any resulting user safety or inconvenience may be prevented.

The correlation may also or instead consider factors such as, for example, any gaps or errors in sensor readings. Such gaps may result from the user sleeping on the same side on which the sensor is implanted, for example. U.S. patent application Ser. No. 13/836,260, filed on Mar. 15, 2013, at paragraphs 191-198, describes measuring impedance to determine tissue compression, changes in the surrounding tissue, and/or properties of the tissue (e.g., % fat, hydration state, compression ischemia, etc.). Accordingly, the electronic device 200 may be configured to correlate compression artifacts with sensor insertion location to determine whether a certain region of the patient (e.g., left side of abdomen) correlates with the most compression artifacts (indicating a likelihood that the patient sleeps on the left side, for example), wherein the electronic device 200 may then recommend a different region (e.g., right side abdomen) for sensor insertions. Similarly, the properties of the tissue at a particular location may not be as well correlated with good sensor performance as compared to the properties of the tissue at a different location, wherein the electronic device 200 may then recommend a particular region that has properties of the tissue correlated with good sensor performance. In another example, U.S. Publ. No. 2012-0265035-A1, at paragraphs 439-448, describes a method of compensating for sensitivity changes based on measured impedance changes, and the specification as a whole describes systems and methods for obtaining diagnostics data. The diagnostics data may be processed by the electronic device 200, to determine patterns that associate diagnostics data with sensor insertion location, wherein the patterns may be used to identify and recommend sensor insertion locations wherein the diagnostics data indicates good sensor reliability and/or performance. In another example, U.S. Pat. No. 8,423,113 describes methods of detecting signal artifacts and replacing signal artifacts. Signal artifacts (e.g., levels of accuracy/confidence/signal artifacts) as described in U.S. Pat. No. 8,010,174 may be correlated with sensor performance, which data may be used to identify sensor insertion locations with greater or lesser levels of accuracy/confidence/signal artifacts, etc. The entire disclosures of the foregoing (U.S. Publ. No. 2014-0005509-A1, U.S. Pat. Nos. 8,010,174, and 8,423,113) are hereby incorporated by reference herein.

The correlated data may be stored in the electronic device, such as in storage 212. The correlated data may also be transmitted to a database. The data may be transmitted anonymously, or may include identifying information about the user. The database may include other correlated data associated with other users. Information from the database may be provided to various users. For example, the database may transmit information to a user who is about to begin a new sensor session. The information may include one or more suggestions of sensor insertion locations that have achieved good results for other users in the database, where the good results may comprise high sensor accuracy, long sensor session length, comfort, completeness of data capture, or the like.

The present embodiments contemplate numerous techniques for determining sensor accuracy for a given sensor session. For example, U.S. Patent Application Publication No. 2009/0192366, at paragraph 441, describes "an evaluation module, also referred to as the processor module, [that] evaluates a predictive accuracy of the calibration information. The term "predictive accuracy" refers without limitation to a measure of how accurate or indicative calibration information is to a true correlation between the analyte signal and the actual analyte concentration, for example, a measure of how well a matched data pair, a plurality of matched data pairs, a calibration set, and/or a calibration line will accurately predict (i.e., estimate/correlate) glucose concentration from a sensor signal across a physiologically relevant range of glucose concentrations (e.g., between about 30 mg/dL and 600 mg/dL of glucose concentration)." In another example, U.S. Pat. No. 8,260,393, at column 81, lines 56-64, describes "a self-diagnostics module, also referred to as a fail-safe module, [that] performs one or more calculations to determine the accuracy, reliability, and/or clinical acceptability of the sensor data. Some examples of the self-diagnostics module are described above, with reference block 556. The self-diagnostics module can be further configured to run periodically (e.g. intermittently or in response to a trigger), for example, on raw data, filtered data, calibrated data, predicted data, and the like." In another example, U.S. Pat. No. 8,260,393, at column 79, lines 35-42, describes "the acceptability is determined by a quality evaluation, for example, calibration quality can be evaluated by determining the statistical association of data that forms the calibration set, which determines the confidence associated with the conversion function used in calibration and conversion of raw sensor data into estimated analyte values. See, e.g. U.S. Publ. No. 2005-0027463-A1." In another example, U.S. Publ. No. 2013-0245401-A1, recites "[o]ne metric useful for determining much of the total error in the system is due to drift is to determine a ratio of the relative error (e.g., smoothed error) at calibration to the absolute error at calibration, and use an absolute value of that ratio for n (or to determine n). In the initial calculation of the ratio RelativeError and AbsoluteError may use seed values, after which the previous estimate may be used in the following equations: $RelativeError_N = Beta*ErrorAtCal + (1-Beta)*RelativeError_{N-1}$ and $AbsoluteError_N = Beta*|ErrorAtCal| + (1-Beta)*AbsoluteError_{N-1}$, where Beta is a forgetting factor for these equations." In another example, sensor accuracy may be defined by a confidence in the sensor data based on an end-of-life detection and/or outlier detection, as described in U.S. Publ. No. 2014-0182350-A1. In another example, sensor accuracy may be defined by a level of certainty, as described in U.S. Publ. No. 2014-0278189-A1. The entire disclosures of the foregoing (U.S. Publ. No. 2009-0192366-A1, U.S. Pat. No. 8,260,393, US 2005-0027463-A1, U.S. Publ. No. 2013-0245401-A1, U.S. Publ. No. 2014-0182350-A1, and U.S. Publ. No. 2014-0278189-A1) are hereby incorporated by reference herein.

In certain embodiments, a pattern analysis may be performed that correlates quantitative data with each insertion location. The quantitative data may embody any of the examples described above, for example sensor accuracy and/or sensor session length. Pattern analyses may be performed by the electronic device 200, by one or more other devices, such as one or more cloud-based processors/servers, and/or by the electronic device 200 in conjunction with one or more other devices.

Pattern analyses may be presented to the user and/or stored in a database. The pattern analyses may be based on information specific to the user, and/or based on information of other users in a database. The pattern analyses may be used to make recommendations to the user about future sensor insertion locations, and/or to provide the user with feedback. The pattern analyses may be presented to the user in various formats, such as a ranked list, a graph, a histogram, a diagram of a body with a heat map, etc.

Any of a wide variety of algorithms that correlate and/or identify patterns may be used with the embodiments described herein. Once the system has sufficient data about previous sensor insertion location (of the patient or a group of patients), pattern recognition may be used to identify patterns or trends associated with insertion site locations and/or may be used to recommend insertion site(s). Some example mathematical approaches include regression, sequence labeling, parsing, neural network-based mapping, fuzzy logic-based pattern matching, Bayesian learning, and Genetic-Algorithms-based pattern matching. Additional considerations, such as a necessary rotation of insertion sites to avoid scarring, may also be included in determining a recommended next insertion site and/or rotation of insertion sites.

In certain embodiments, the electronic device may prompt the user to input personal information. The personal information may include, for example, at least one of height, weight, age, sex, body mass index (BMI), the user's current location, the user's current mood, the user's current pain level, the user's current comfort level, the user's current confidence level, the user's perception of sensor performance, a location of an insulin infusion pump relative to the sensor, adhesive irritation, if any, adhesive success rate (when the adhesive started to peel or when the sensor fell off), how much daily insulin used by the user, type of insulin, level of exercise/activity, current weather, etc. The electronic device may use the personal information to provide an additional level of correlation between the sensor performance and the insertion site. Based on the input data, the algorithm can suggest, for example, that a 35 year old male should insert the sensor in the abdominal area, while a 45 year old woman should insert the sensor in the triceps area.

Certain personal information, such as the user's confidence level, comfort level, mood, and overall perception of the sensor insertion process, might influence, or set the user's expectations for that sensor's performance as well as future sensor performance. This data can be beneficial for several reasons, including better understanding of user expectations, users can see if their wear experience was better or worse than their initial expectations, a CGM application can suggest insertion sites with which the user may feel more comfortable, etc. This information can also be helpful in correlating user perceptions on accuracy with actual sensor data measurements. Data relating to adhesive issues can help identify issues with a certain lot of adhesive, which issue(s) may be correlated by time of year, environmental factors, etc.

In certain embodiments, the electronic device may determine the user's BMI based on information input by the user, such as his or her height and weight. In alternative embodiments, the sensor and/or structure associated with the sensor may include one or more electrodes for measuring the user's BMI at the sensor insertion location.

Figure 4:
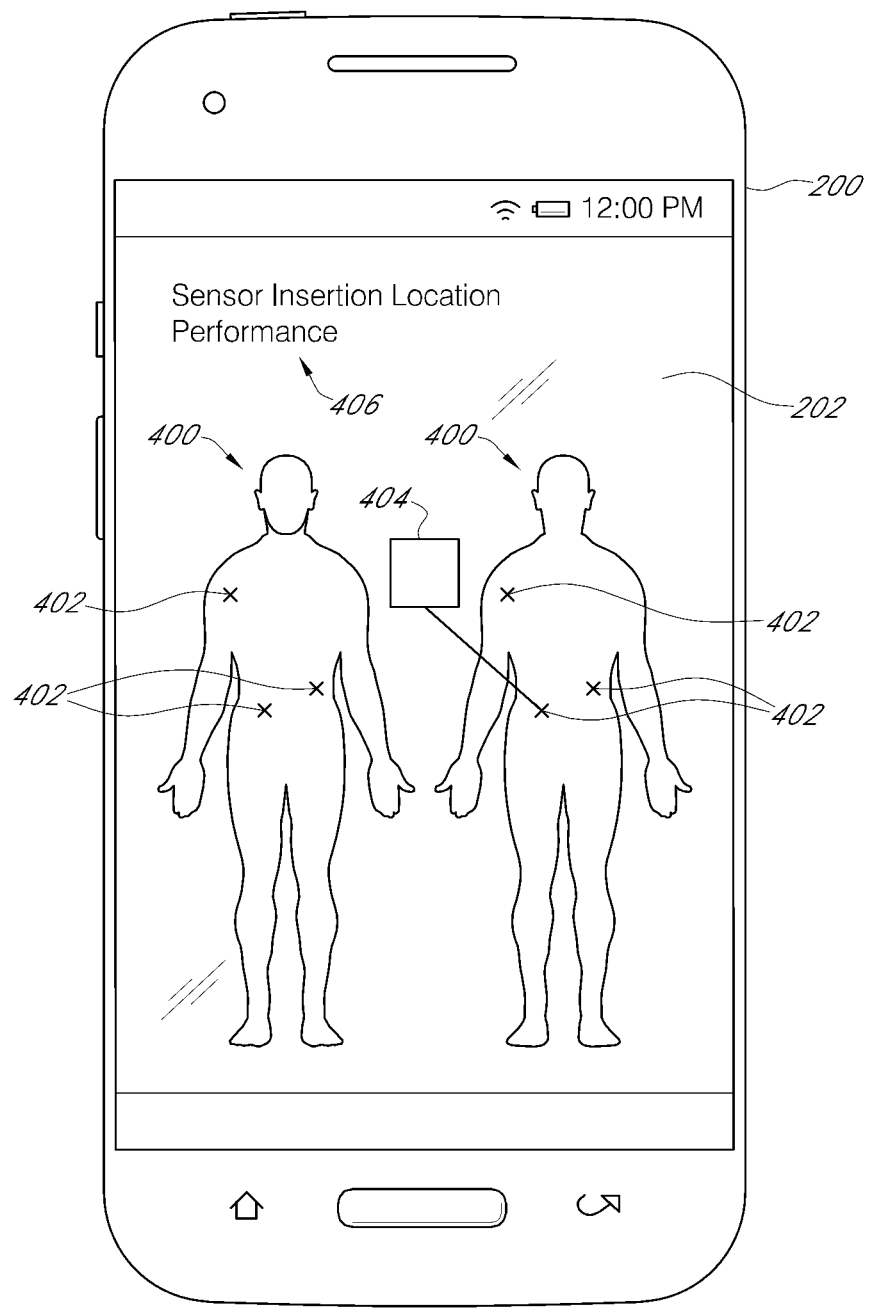

In certain embodiments, the electronic device 200 and/or other devices, such as cloud-based devices, may store data pertaining to previous sensor sessions. For example, with reference to FIG. 4, the display 202 may show a diagram 400 of a body that is annotated with data about previous sensor locations 402. Each of the previous sensor locations 402 may include textual information about that location, such as a date when a sensor was inserted at each location, quantitative data about that location, and/or information about the user's activity level during each sensor session. The quantitative data may embody any of the examples described above, for example sensor accuracy and/or sensor session length. The information about previous sensor sessions may comprise information stored on the electronic device 200, and which is based on previous sensor sessions for the user of that particular electronic device 200. Alternatively, or in addition, the information about previous sensor sessions may comprise information downloaded to the electronic device 200 from a database, which information is based upon previous sensor sessions of users in the database, which may include information about the user of that particular electronic device 200. The information from the database may be organized by various characteristics, such as age, sex, BMI, etc.

The textual information may be provided in one or more popup boxes 404, which may all appear on the screen at the same time, or which may appear one-by-one as the user selects successive ones of the previous sensor locations 402. In certain embodiments, instead of or in addition to the textual information, each previous sensor location 402 may be graphically categorized, such as color-coded. For example, locations 402 that have been associated with good sensor performance in the past may be a first color, such as green, while locations 402 that have been associated with bad sensor performance in the past may be a second color, such as red. The present embodiments are, of course, not limited to only two colors. Any number of colors and/or shades of the same color may be used to indicate past sensor performance. The display 202 may also provide text 406, such as a description of what is being depicted. For example, in FIG. 4 the display 202 indicates that the user is viewing performance data regarding past sensor insertion locations.

Figure 5:
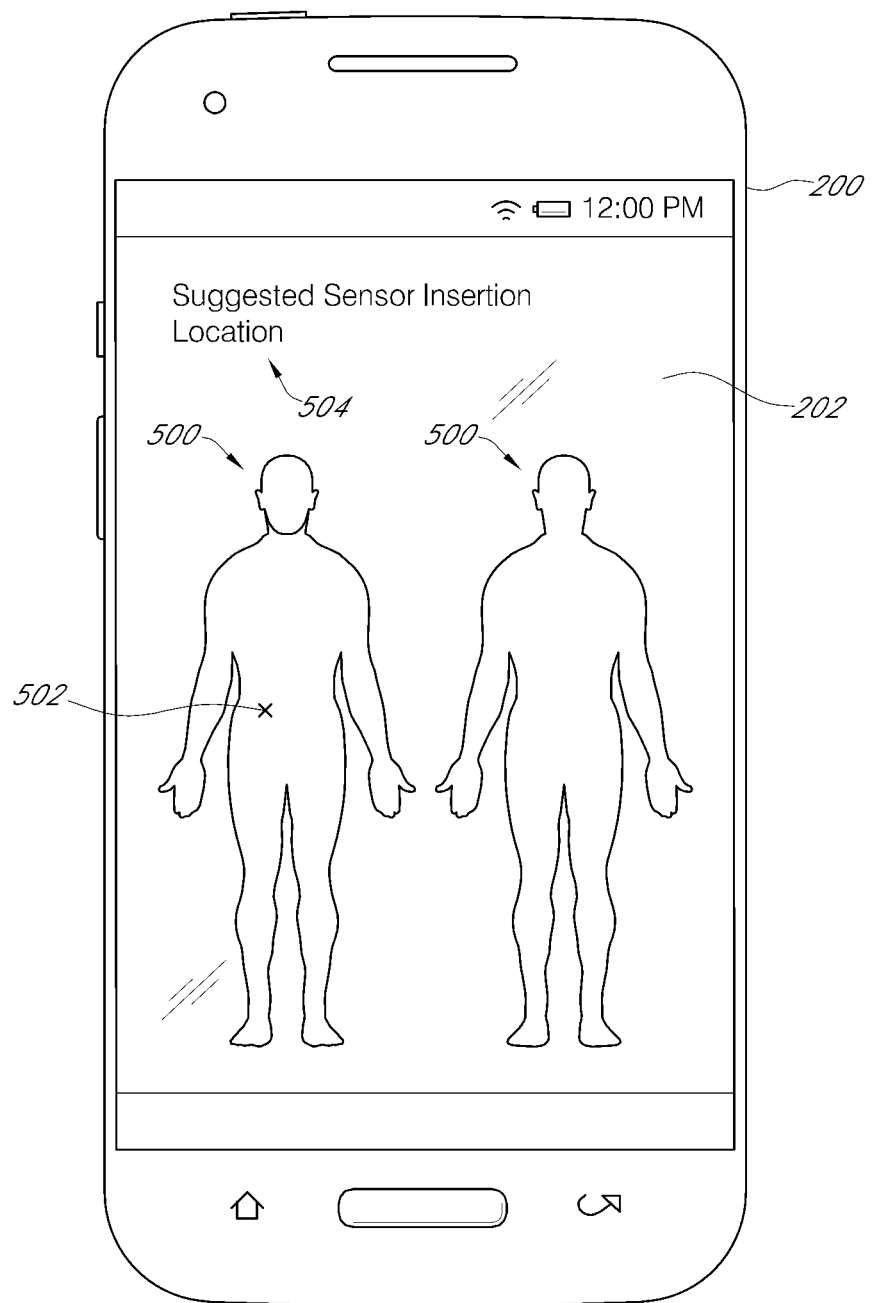

Instead of, or in addition to, the functionality described above, the electronic device 200 may track a user's sensor insertion locations in order to provide the user with a suggested insertion location based on a recommended rotation of locations. For example, the user may be presented a diagram 500 of a body on the display 202, as shown in FIG. 5. The diagram 500 may include only one suggested sensor location 502, which location 502 is based on a recommended rotation of locations. With each successive sensor session, the electronic device 200 suggests the next location 502 in the recommended rotation. The recommended rotation may be based on information stored on the electronic device 200 and/or stored on one or more other devices, such as cloud-based servers. The display 202 may also provide text 504, such as a description of what is being depicted. For example, in FIG. 5 the display 202 indicates that the user is viewing a suggested sensor insertion location 502.

In certain embodiments, the electronic device may suggest a better insertion location based upon data from a current sensor session and/or data of other users in a database. For example, during a sensor session, the system may determine that the sensor is not providing accurate data. The electronic device may prompt the user to remove the current sensor and implant a new one at a new insertion location indicated on the display 202. The new insertion location may be associated with good sensor performance in previous sensor sessions.

In certain embodiments, an application executing on the electronic device may show an outline of a body. A friend of the user, or the user with the aid of a mirror, may then line up the template/outline of a human body over the user. A picture may then be taken to enable the application to know exactly where on the body the sensor is placed.

Figure 6:
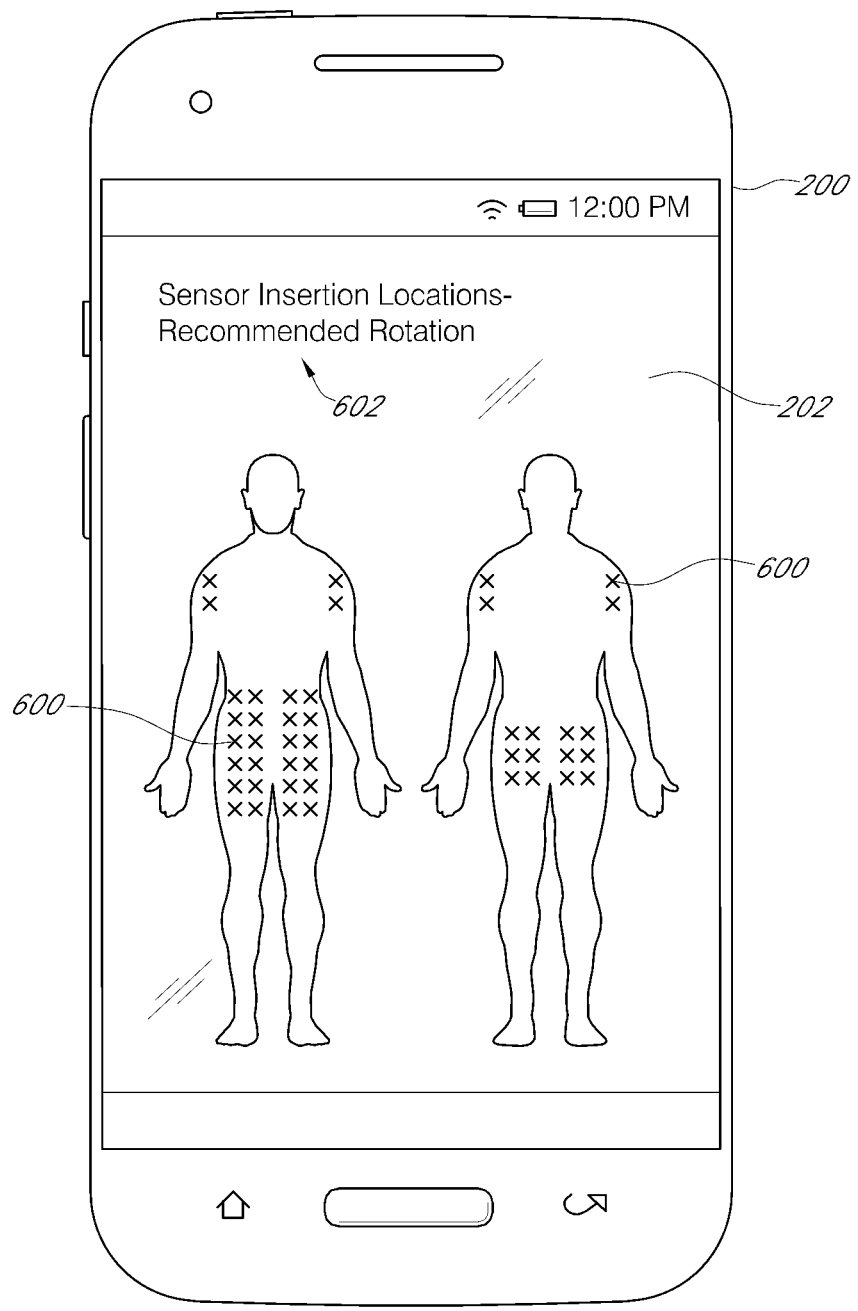

In certain embodiments, the electronic device may display every sensor insertion location 600 in the recommended rotation, as shown in FIG. 6. Each of the insertion locations 600 may be consecutively numbered, and a suggested next insertion location may be highlighted. The display 202 may also provide text 602, such as a description of what is being depicted. For example, in FIG. 6 the display 202 indicates that the user is viewing a recommended rotation of sensor insertion locations 600.

FIGS. 7-12 are flowcharts illustrating various embodiments of methods for continuous analyte monitoring. The various tasks performed in connection with each one of the flowcharts of FIGS. 7-12 may be performed by user action, by a processor executing instructions embodied in a non-transitory computer-readable medium, or by a combination of both. For example, tasks may be performed by hardware, software, firmware, or any combination thereof, incorporated into one or more of the computing devices discussed herein. Any of the flowcharts of FIGS. 7-12 may also include any number of additional or alternative tasks. Further, the tasks shown in FIGS. 7-12 need not be performed in the illustrated order and/or may be incorporated into a more comprehensive procedure or process having additional functionality not described in detail herein.

Figure 7:
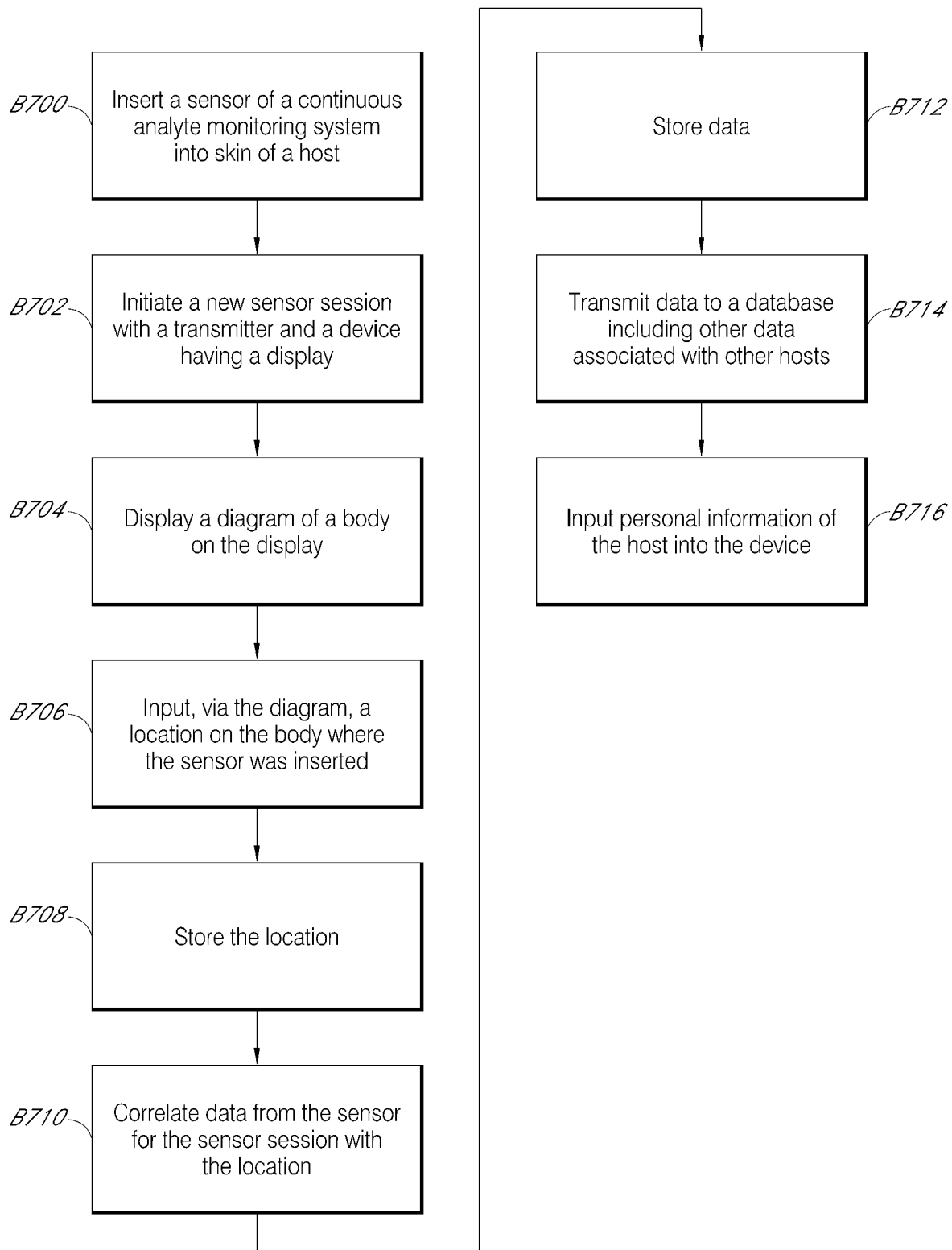
FIGS. 7-14 are flowcharts illustrating various embodiments of methods for continuous analyte monitoring.

With reference to FIG. 7, some embodiments comprise, at block B700, inserting the sensor 10 of the continuous analyte sensor system 8 into skin of a host. At block B702, the method further comprises initiating a new sensor session with the sensor electronics 12 and the device 200 having the display 202. At block B704, the method further comprises displaying the diagram 300 of a body on the display 202. At block B706, the method further comprises inputting, which may be via the diagram 300, a location on the body where the sensor 10 was inserted. At block B708, the method further comprises storing the location, such as storing the location in the storage 212. At block B710, the method may further comprise correlating data from the sensor 10 for the sensor session with the location. The correlating may be done by the electronic device 200, by other devices, such as the cloud-based processor 22 and/or other devices in the network 24, and/or by a combination thereof. At block B712, the method may further comprise storing data, such as storing data in the storage 212. The data may be correlated data, data that has not been correlated, and/or a combination thereof. At block B714, the method may further comprise transmitting data (correlated or uncorrelated) to a database, such as a database in the network 24. The database may include data associated with other hosts. The data may include quantitative data regarding one or more sensor sessions corresponding to one or more sensor insertion locations. The quantitative data may embody any of the examples described above, for example sensor accuracy and/or sensor session length, correlated with each location. The correlation may be with respect to two or more inputs. For example, another input may be avoiding scarring. At block B716, the method may further comprise inputting personal information of the host into the device 200. The personal information may include, for example, at least one of height, weight, age, sex, body mass index (BMI), the user's current mood, the user's current pain level, the user's current comfort level, the user's current confidence level, the user's perception of sensor performance, a location of an insulin infusion pump relative to the sensor, type of insulin, level of exercise/activity, adhesive irritation, if any, adhesive success rate (when the adhesive started to peel or when the sensor fell off), etc.

Figure 8:
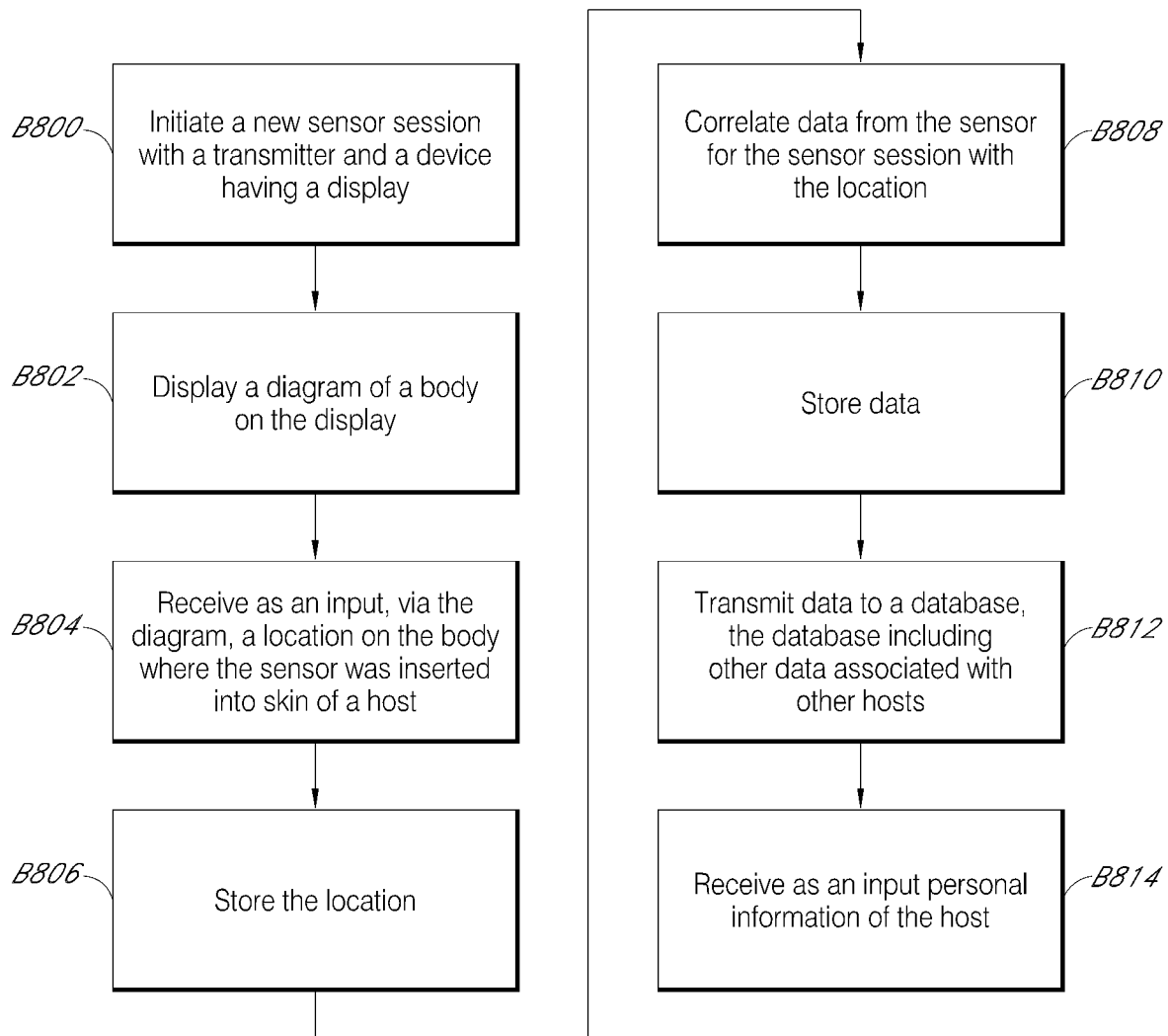

With reference to FIG. 8, some embodiments comprise, at block B800, initiating a new sensor session with the sensor electronics 12 and the device 200 having the display 202. At block B802, the method further comprises displaying a diagram 300 of a body on the display 202. At block B804, the method further comprises receiving as an input, which may be via the diagram 300, a location on the body where the sensor 10 was inserted into skin of a host. At block B806, the method further comprises storing the location, such as storing the location in the storage 212. At block B808, the method may further comprise correlating quantitative data from the sensor 10 (such as the examples of quantitative data described above) for the sensor session with the location. The correlating may be done by the electronic device 200, by other devices, such as the cloud-based processor 22 and/or other devices in the network 24, and/or by a combination thereof. At block B810, the method may further comprise storing data, such as storing data in the storage 212. The data may be correlated data, data that has not been correlated, and/or a combination thereof. At block B812, the method may further comprise transmitting data (correlated or uncorrelated) to a database, such as a database in the network 24. The database may include data associated with other hosts. The data may include quantitative data regarding one or more sensor sessions corresponding to one or more sensor insertion locations. The quantitative data may include any of the examples of quantitative data described above correlated with each location. The correlation may be with respect to two or more inputs. For example, another input may be avoiding scarring. At block B814, the method may further comprise receiving as an input personal information of the host. The personal information may include, for example, at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, if any, adhesive success rate (when the adhesive started to peel or when the sensor fell off), etc.

Figure 9:
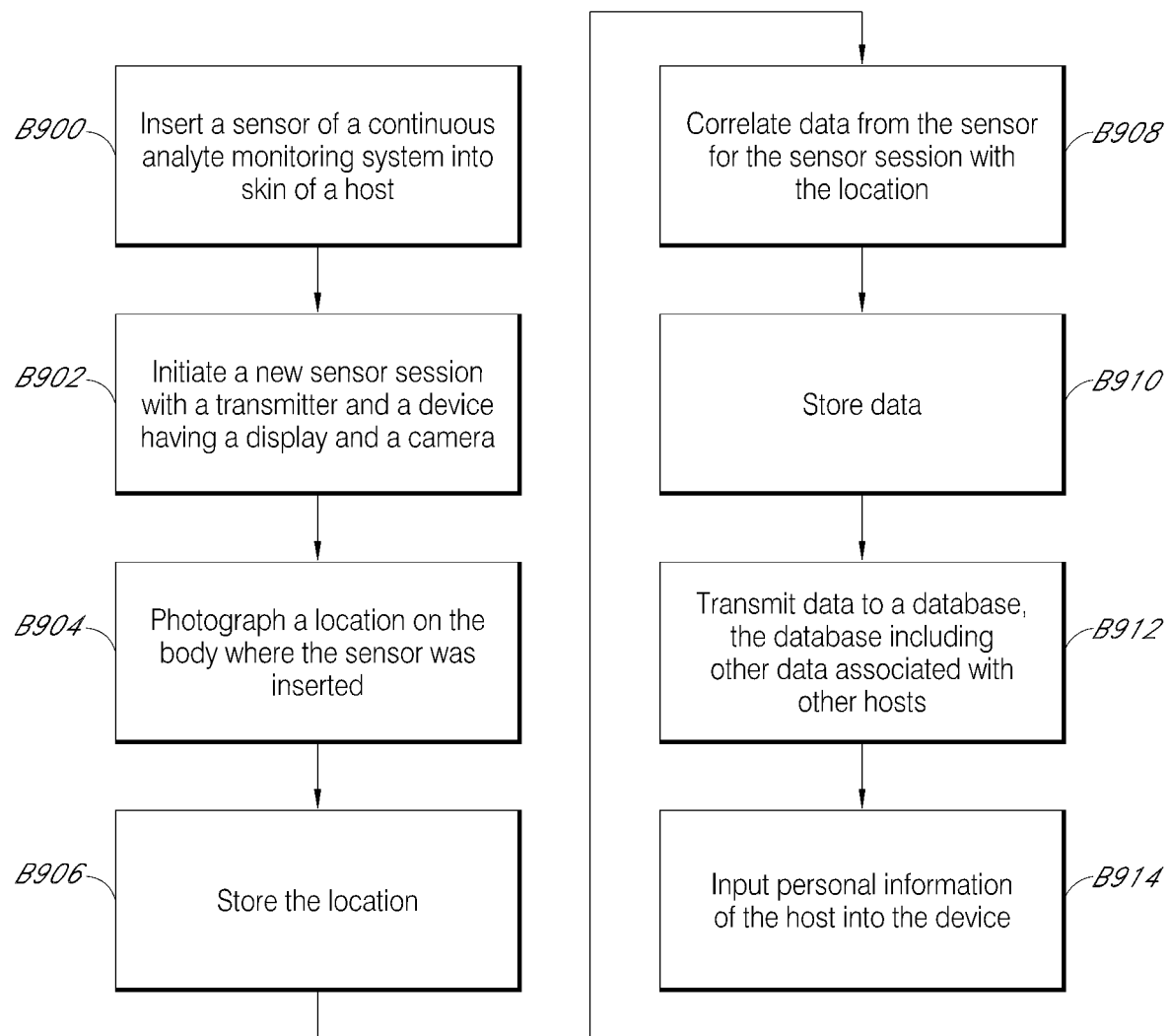

With reference to FIG. 9, some embodiments comprise, at block B900, inserting the sensor 10 of the continuous analyte sensor system 8 into skin of a host. At block B902, the method further comprises initiating a new sensor session with the sensor electronics 12 and the device 200 having the display 202 and a camera. At block B904, the method further comprises photographing a location on the body where the sensor 10 was inserted. For example, the photograph may be taken with a camera of the device 200. At block B906, the method further comprises storing the location, such as storing the location in the storage 212. At block B908, the method may further comprise correlating quantitative data from the sensor 10 (such as the examples of quantitative data described above) for the sensor session with the location. The correlating may be done by the electronic device 200, by other devices, such as the cloud-based processor 22 and/or other devices in the network 24, and/or by a combination thereof. At block B910, the method may further comprise storing data, such as storing data in the storage 212. The data may be correlated data, data that has not been correlated, and/or a combination thereof. At block B912, the method may further comprise transmitting data (correlated or uncorrelated) to a database, such as a database in the network 24. The database may include data associated with other hosts. The data may include quantitative data regarding one or more sensor sessions corresponding to one or more sensor insertion locations. The quantitative data may include any sensor information described elsewhere herein, such as sensor accuracy correlated with each location, and/or sensor session length correlated with each location. The correlation may be with respect to two or more inputs. For example, another input may be avoiding scarring. At block B914, the method may further comprise inputting personal information of the host into the device 200. The personal information may include, for example, at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, if any, adhesive success rate (when the adhesive started to peel or when the sensor fell off), etc.

Figure 10:
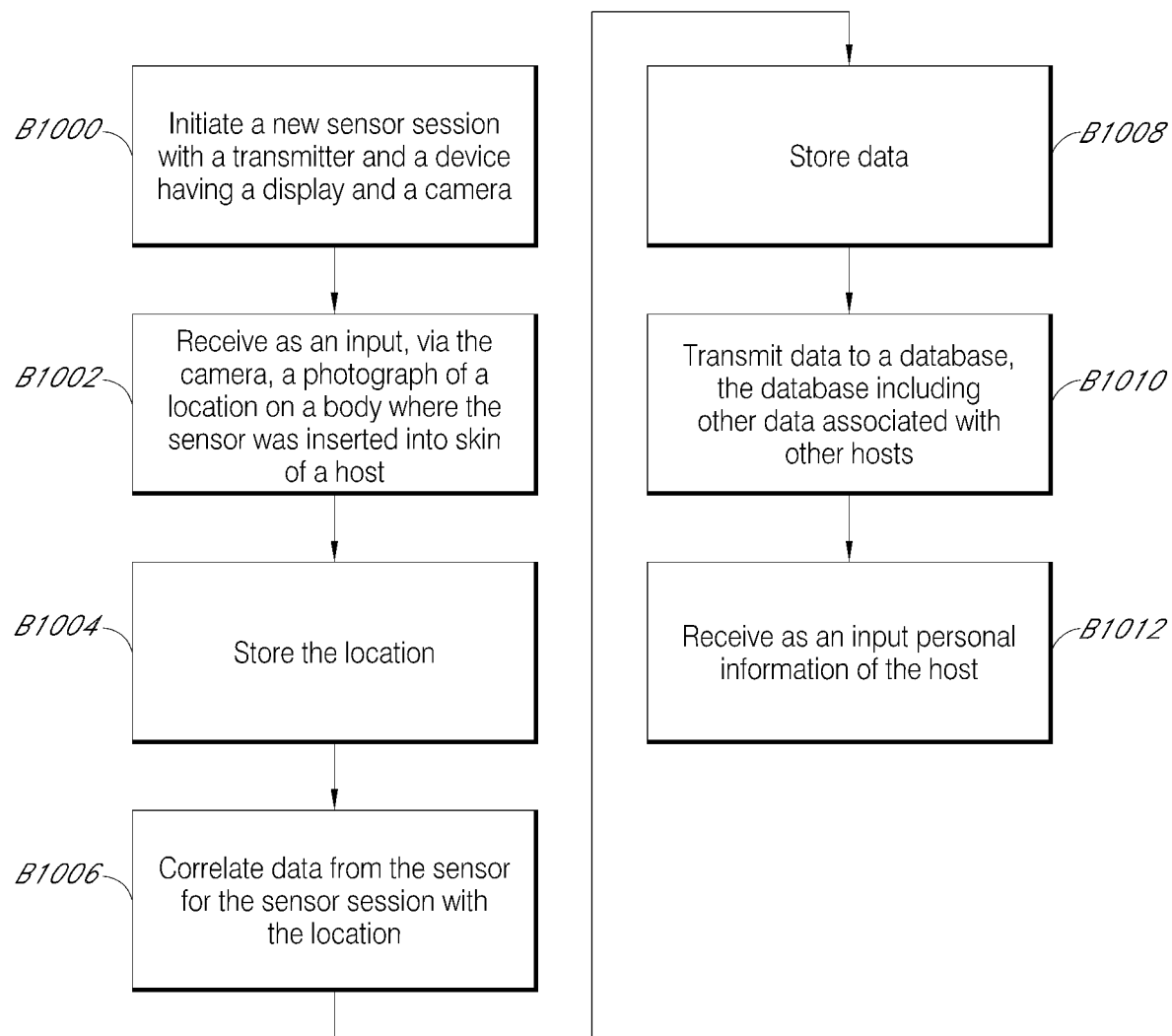

With reference to FIG. 10, some embodiments comprise, at block B1000, initiating a new sensor session with the sensor electronics 12 and the device 200 having the display 202 and a camera. At block B1002, the method further comprises receiving as an input, via the camera, a photograph of a location on a body where the sensor 10 was inserted into skin of a host. In some embodiments, the location may be determined by digital signal analysis performed on the photograph. At block B1004, the method further comprises storing the location, such as storing the location in the storage 212. At block B1006, the method may further comprise correlating data from the sensor 10 for the sensor session with the location. The correlating may be done by the electronic device 200, by other devices, such as the cloud-based processor 22 and/or other devices in the network 24, and/or by a combination thereof. At block B1008, the method may further comprise storing data, such as storing data in the storage 212. The data may be correlated data, data that has not been correlated, and/or a combination thereof. At block B1010, the method may further comprise transmitting data (correlated or uncorrelated) to a database, such as a database in the network 24. The database may include data associated with other hosts. The data may include quantitative data regarding one or more sensor sessions corresponding to one or more sensor insertion locations. The quantitative data may include any of the examples described above, for example sensor accuracy and/or sensor session length, correlated with each location. The correlation may be with respect to two or more inputs. For example, another input may be avoiding scarring. At block B1012, the method may further comprise receiving as an input personal information of the host. The personal information may include, for example, at least one of height, weight, age, sex, body mass index (BMI), the user's current mood, the user's current pain level, the user's current comfort level, the user's current confidence level, the user's perception of sensor performance, a location of an insulin infusion pump relative to the sensor, adhesive irritation, if any, adhesive success rate (when the adhesive started to peel or when the sensor fell off), etc.

Figure 11:
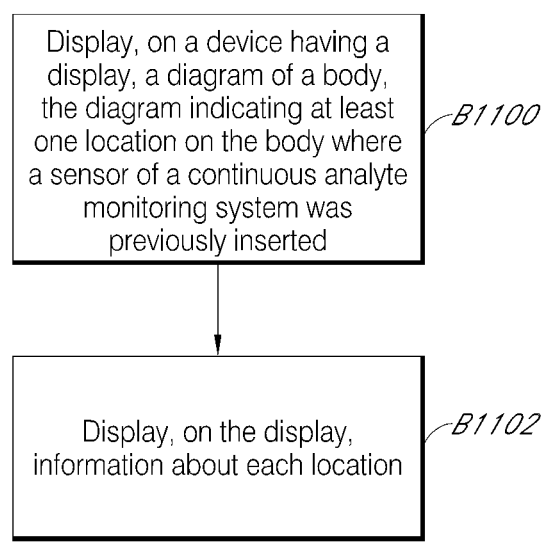

With reference to FIG. 11, embodiments comprise, at block B1100, displaying, on the device 200 having the display 202, a diagram 400 of a body, the diagram indicating at least one location 402 on the body where the sensor 10 of the continuous analyte sensor system 8 was previously inserted. At block B1102, the method further comprises displaying, on the display 202, information about each location 402. The information may include a date when the sensor 10 was inserted at each location 402. The information may include quantitative data regarding one or more sensor sessions corresponding to each sensor insertion location 402. The quantitative data may include any of the examples described above, for example sensor accuracy and/or sensor session length correlated with each location 402.

Figure 12:
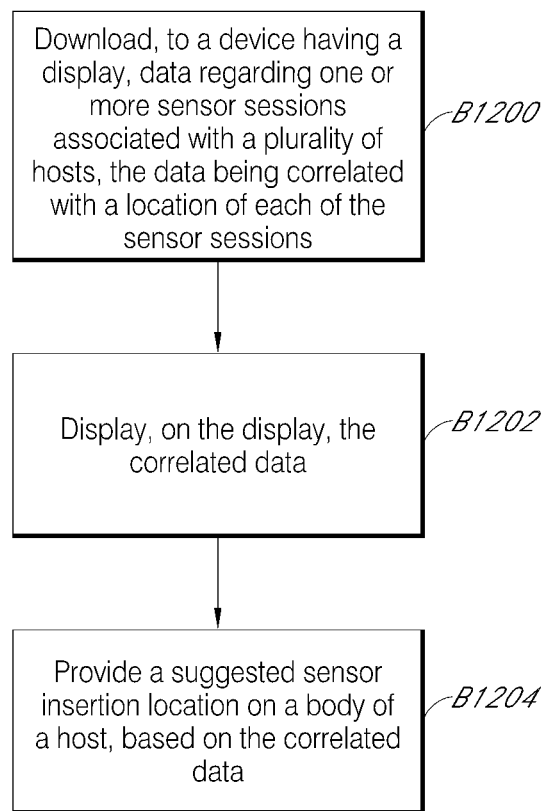

With reference to FIG. 12, some embodiments comprise, at block B1200, downloading, to the device 200 having the display 202, data regarding one or more sensor sessions associated with a plurality of hosts, the data being correlated with a location of each of the sensor sessions. At block B1202, the method further comprises displaying, on the display 202, the correlated data. At block B1204, the method may further comprise providing a suggested sensor insertion location 502 on a body of a host, based on the correlated data. The correlated data may include any of the examples of quantitative data described above, for example sensor accuracy correlated with each location, and/or sensor session length correlated with each location.

In some example embodiments, a sensor insertion site may be selected based on a particular fault mode, such as "dip and recover." The phenomenon known as "dip and recover" is a fault mode including a suppressed signal characteristic that is experienced by some patients during early sensor wear. This fault mode is described in detail in U.S. Publ. No. 2014-0005505-A1, which is incorporated herein by reference in its entirety and made a part of this disclosure. In this example, a user can select an insertion site with the least likelihood of experiencing the "dip and recover" phenomenon, which may be related to insertion site. For example, a processor of an electronic device (such as the processor 208 of the electronic device 200) may query a database, such as a database in the network 24, to determine a sensor insertion site with the least probability of experiencing "dip and recover." The database may be patient-specific (e.g. contain data specific to that user), or the database may contain data pertaining to a population of users.

In some example embodiments, a sensor insertion site may be selected based on nighttime hypoglycemic reliability and/or accuracy. For example, a processor of an electronic device (such as the processor 208 of the electronic device 200) may analyze data in the hypoglycemic range, where the data is gathered during nighttime hours. The data may be specific to that patient, or may pertain to a population of patients. Reliability and accuracy may be based on reliability metrics and accuracy metrics, respectively.

In some example embodiments, the determination of sensor insertion site location, and associated algorithmic analysis, may be optimized for a particular patient use. For example, insertion site location and algorithmic analysis may be optimized for time of day, hypoglycemic accuracy, reduction of a particular fault mode, etc.

Figure 13:
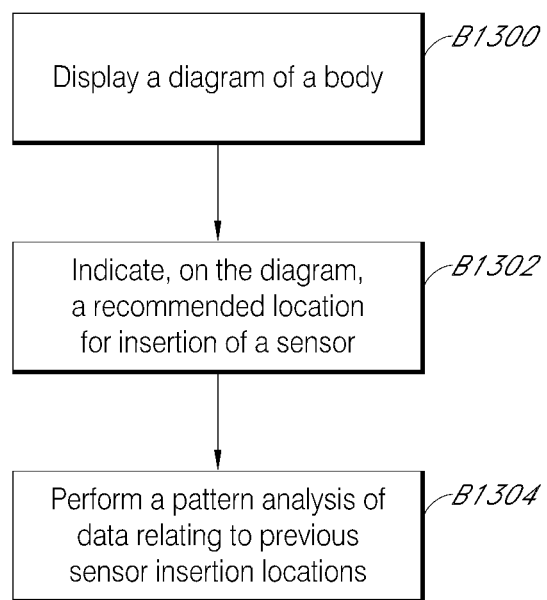

With reference to FIG. 13, some embodiments comprise, at block B1300, displaying, on the device 200 having the display 202, a diagram 300 of a body. At block B1302, the method further comprises indicating, on the diagram 300, a recommended location 600 for insertion of the sensor 10. At block B1304, the method may further comprise performing a pattern analysis of data relating to previous sensor insertion locations. The data may include data pertaining to at least one other user.

Figure 14:
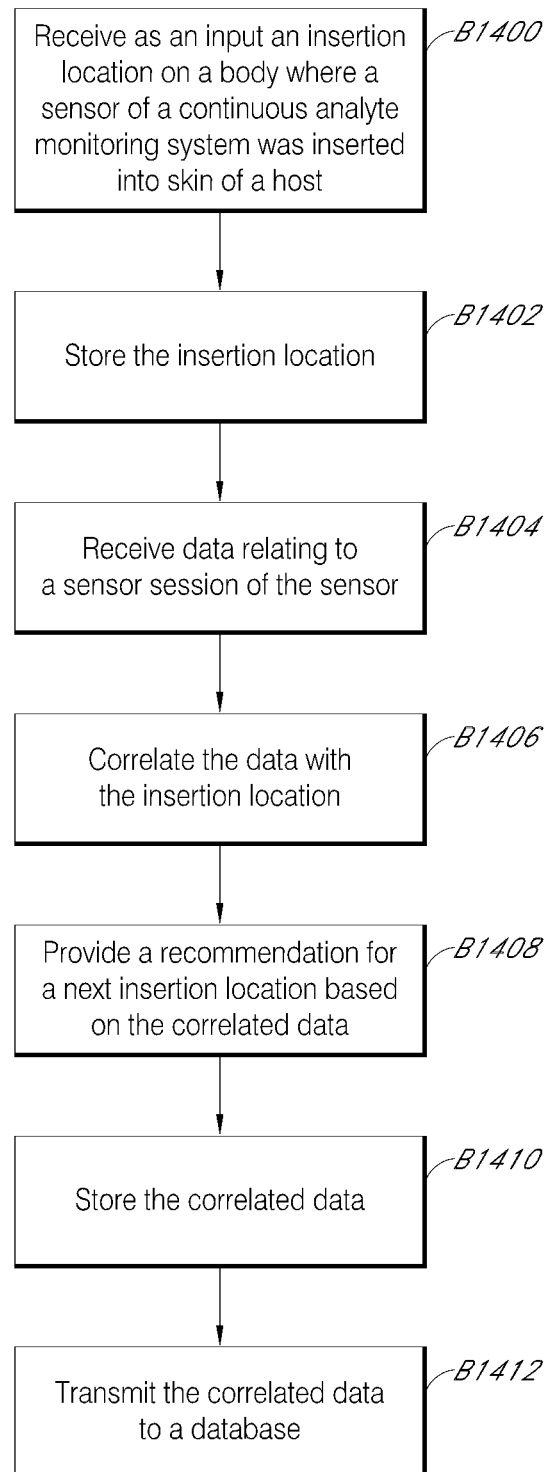

With reference to FIG. 14, some embodiments comprise, at block B1400, receiving as an input an insertion location on a body where the sensor 10 of the continuous analyte sensor system 8 was inserted into skin of a host. At block B1402, the method further comprises storing the insertion location, such as storing the insertion location in the storage 212. At block B1404, the method further comprises receiving as inputs data relating to a sensor session of the sensor 10. At block B1406, the method further comprises correlating the data with the insertion location. At block B1408, the method may further comprise providing a recommendation for a next insertion location 600 based on the correlated data. At block B1410, the method may further comprise storing the correlated data, such as storing the correlated data in the storage 212. At block B1412, the method may further comprise transmitting the correlated data to a database, such as a database in the network 24. The database may include other correlated data associated with other hosts.

Figure 15:
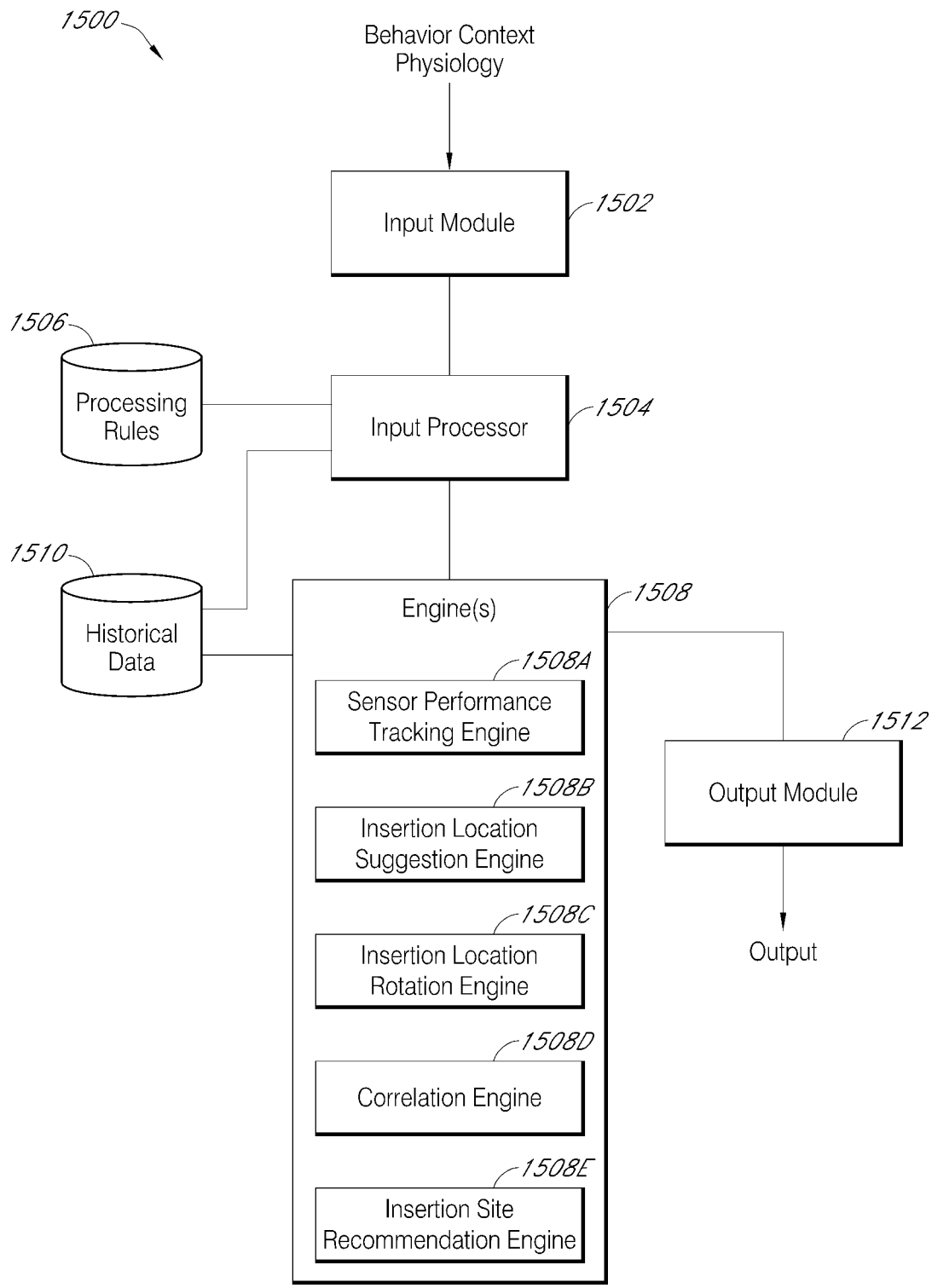
FIG. 15 is a functional block diagram for a continuous analyte monitoring system including features described herein.

FIG. 15 is a functional block diagram for a continuous analyte monitoring system 1500 including features described herein. The system 1500 may be implemented using any of the systems described herein, including any of those described with respect to FIGS. 1, 2A, 2B, and 3-6. The system 1500 includes an input module 1502, which may be, for example, any computer, any of the devices described herein that are capable of receiving input, including any of the devices described with respect to FIGS. 1, 2A, 2B, and 3-6, and/or be incorporated into any of these devices. The input module 1502 is configured to obtain any of the inputs described herein, including any behavior, context and physiological inputs associated with a user. The inputs may be received from a user via manual input using a user interface, sensors (e.g., biometric sensors, geographic positioning sensors, etc.), information systems (e.g. external health-data databases), social media, voice response, actions on the system 1500 (e.g., search), and any other inputs described herein. The input module 1502 may include wired (e.g., Ethernet, USB, HDMI, coaxial cable, telephonic, patch cabling, fiber optic cable) or wireless (e.g., WiFi, Bluetooth) communication channels for requesting and/or receiving the inputs.

FIG. 15, the input module 1502 is coupled with an input processor 1504 configured to process the received inputs. Processed inputs may be also be added over time to a historical database 1510 for use in future processing. The historical database 1510 is described in further detail below. The input processor 1504 may comprise, for example, a cloud-based processor 22 such as that described with respect to FIG. 1, a processor 208 such as that described with respect to FIG. 2B, or any other processor. The input processor 1504 may be configured to process the received inputs based on processing rules obtained from a processing rules database 1506. The input processor 1504 may receive the input data along with the source of the data. Based on the source, a processing rule may be selected from the processing rules database 1506. The processing rules may indicate a format for the input data, an appropriate parser, or other information to facilitate extraction and categorization of the information included in the input data.

The input processor 1504 may provide the extracted information to one or more engines 1508. The engines 1508 are configured to perform processing related to any of the processes described above. For example, one engine 1508 may comprise a sensor performance tracking engine 1508A, which is configured to track sensor performance as described above with respect to FIGS. 3 and 4. Another engine 1508 may comprise an insertion location suggestion engine 1508B, which is configured to provide the user with a suggested location for insertion of a sensor based upon past sensor performance in various insertion locations, as described above with respect to FIG. 5. Another engine 1508 may comprise an insertion location rotation engine 1508C, which is configured to provide the user with a suggested location for insertion of a sensor based upon a planned rotation of insertion locations, as described above with respect to FIG. 6.

Another engine 1508 may comprise a correlation engine 1508D, which is configured to perform the correlating described herein. For example, the correlation engine 1508D may perform the correlations described with respect to boxes B710 (FIG. 7), B808 (FIG. 8), B908 (FIG. 9), B1006 (FIG. 10), and B1406 (FIG. 14), as well as pattern analysis as discussed with respect to B1304 of FIG. 13. Another engine 1508 may comprise an insertion site recommendation engine 1508E, which is configured to perform the insertion site recommendations described herein. For example, the insertion site recommendation engine 1508E may perform the insertion site recommendations described with respect to box B1204 (FIG. 12).

The engines 1508 may be in data communication with a historical database 1510. The historical database 1510 can include past input information associated with the user and/or aggregated information associated with other users (e.g., big data analytics for a community of similarly situated users). Engines 1508 can use this information to perform the functions associated with each engine.

The system 1500 further includes an output module 1512. The output module 1512 may receive outputs from the engines 1508 and display and/or transmit the outputs. For example, the output can include insertion location suggestions to the user, and/or reports indicating performance of insertion locations tracked by the system as discussed herein. The output module 1512 may include a display and/or wired (e.g., Ethernet, USB, HDMI, coaxial cable, telephonic, patch cabling, fiber optic cable, etc.) and/or wireless (e.g., WiFi. Bluetooth, etc.) communication means for transmitting the outputs.

The connections between the elements shown in FIG. 15 illustrate example communication paths for the system 1500. Additional communication paths, either direct or via an intermediary, may be included to further facilitate the exchange of information for the system 1500. The communication paths may be bi-directional communication paths allowing the elements shown to exchange information.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus, and/or device (e.g., magnetic disks, optical disks, memory, programmable logic devices (PLDs)) used to provide machine instructions and/or data to a programmable processor, including a machine-readable medium that receives machine instructions.

While specific examples have been provided herein for illustrative purposes, it is understood that to provide for interaction with a user, the subject matter described herein may be implemented on a computer having a display device (e.g., a CRT (cathode ray tube), LED (light-emitting diode), or LCD (liquid crystal display) monitor) for displaying information to the user and a keyboard and a pointing device (e.g., a mouse or a trackball) by which the user may provide input to the computer. Other kinds of devices may be used to provide for interaction with a user as well, for example, feedback provided to the user may be any form of sensory feedback (e.g., visual feedback, auditory feedback, or tactile feedback), and input from the user may be received in any form, including acoustic, speech, or tactile input.

Further, while specific examples have been provided herein for illustrative purposes, it is understood that the subject matter described herein may be implemented wholly or in part using a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

It should be appreciated that all methods and processes disclosed herein may be used in any analyte monitoring system, continuous or intermittent. It should further be appreciated that the implementation and/or execution of all methods and processes may be performed by any suitable devices or systems, whether local or remote. Further, any combination of devices or systems may be used to implement the present methods and processes.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of initiating a new sensor session with a transmitter of a continuous analyte monitoring system and a device, comprising:
displaying, on a display of the device, a diagram of a body, the diagram indicating one or more sensor locations on the diagram;
displaying, on the display of the device, information about the one or more sensor locations; and
after displaying the information about the one or more sensor locations, initiating the new sensor session with the device and the transmitter of the continuous analyte monitoring system whose sensor is inserted into a sensor location on a patient body during the new sensor session.

2. The method of claim 1, wherein the information comprises textual information about at least one of the one or more sensor locations.

3. The method of claim 2, wherein the textual information comprises text indicating that performance data about the at least one of the one or more sensor locations is being displayed, a date when the sensor was inserted at the at least one of the one or more sensor locations, quantitative data about the at least one of the one or more sensor locations, or information about activity level of a patient associated with the device during a respective sensor session corresponding to the at least one of the one or more sensor locations.

4. The method of claim 3, wherein the textual information comprises quantitative data about the respective sensor location, the quantitative data comprising sensor accuracy, or sensor session length.

5. The method of claim 2, wherein the information comprises textual information about each of the one or more sensor locations, and wherein the textual information is presented with one or more popup boxes corresponding to the one or more sensor locations.

6. The method of claim 5, wherein all of the one or more popup boxed are displayed simultaneously.

7. The method of claim 5, wherein only one popup box is displayed at a time in response to user input selecting a corresponding one of the one or more sensor locations.

8. The method of claim 1, wherein each of the one or more sensor locations displayed on the diagram is graphically categorized.

9. The method of claim 8, wherein a first group of the one or more sensor locations are graphically categorized in a first performance category and a second group of the one or more sensor locations are graphically categorized in a second performance category, wherein the first performance category indicates a better sensor performance than the second performance category.

10. The method of claim 9, wherein the first group is graphically categorized and displayed with a first color and the second is graphically categorized and displayed with a second color.

11. The method of claim 9, further comprising receiving user input at the device, the user input indicative of the sensor location being used for the new sensor session, wherein the sensor location is one of the first group of the one or more sensor locations graphically categorized in the first performance category.

12. The method of claim 1, further comprising:
tracking performance data associated with one or more sensor sessions corresponding to the one or more sensor locations to generate the information about the one or more sensor locations.

13. The method of claim 1, further comprising:
determining to recommend the sensor location to be used for inserting the sensor into for establishing the new sensor session
displaying, on the display of the device, a recommendation for the sensor location.

14. The method of claim 13, further comprising receiving user input at the device, the user input indicative of the sensor location being used for the new sensor session.

15. The method of claim 13, wherein the determining is based on a rotation of sensor locations, wherein the one or more sensor locations exclude the sensor location.

16. The method of claim 15, wherein each of the one or more sensor locations is consecutively numbered on the diagram, and wherein the sensor location is displayed as a recommended next insertion location, wherein the recommendation indicates the recommended next insertion location.

17. The method of claim 1, wherein the one or more sensor locations exclude the sensor location.

18. The method of claim 1, wherein the one or more sensor locations include the sensor location.

19. The method of claim 1, further comprising:
displaying, on the display, a body outline;
capturing, at the device, an image of the patient body while the body outline is lined up with the patient body on the display, the image showing where on the patient body the sensor is inserted into during the new sensor session; and
identifying, at the device, the sensor location based on the image.

20. A system for continuous analyte monitoring, comprising:
a continuous analyte monitoring system, comprising:
an analyte sensor configured to be inserted into skin of a host for measuring analyte levels of a patient;
a transmitter communicatively coupled to the analyte sensor, the transmitter being configured to receive analyte measurements from the analyte sensor and transmit analyte data based on the analyte measurements to a processor;
a memory comprising executable instructions;
a display;
the processor in data communicating with the memory and configured to execute the instructions to:
display, on the display, a diagram of a body, the diagram indicating one or more sensor locations on the diagram;
display, on the display of the device, information about the one or more sensor locations; and initiate, after the information is displayed, a new sensor session with the device and the transmitter of the continuous analyte monitoring system whose sensor is inserted into a sensor location on a patient body during the new sensor session.

* * * * *